(12) United States Patent
Noda et al.

(10) Patent No.: US 11,199,682 B2
(45) Date of Patent: Dec. 14, 2021

(54) IMAGING OPTICAL SYSTEM AND IMAGE CAPTURING APPARATUS

(71) Applicant: TAMRON CO., LTD., Saitama (JP)

(72) Inventors: Takayuki Noda, Saitama (JP); Yasuhiko Obikane, Saitama (JP)

(73) Assignee: TAMRON CO., LTD., Saitama (JP)

( * ) Notice: Subject to any disclaimer, the term of this patent is extended or adjusted under 35 U.S.C. 154(b) by 198 days.

(21) Appl. No.: 16/594,643

(22) Filed: Oct. 7, 2019

(65) Prior Publication Data
US 2020/0271896 A1  Aug. 27, 2020

(30) Foreign Application Priority Data

Feb. 27, 2019  (JP) .............. JP2019-034347

(51) Int. Cl.
| | | |
|---|---|---|
| *G02B 9/60* | (2006.01) | |
| *G02B 13/00* | (2006.01) | |
| *G02B 23/24* | (2006.01) | |
| *A61B 1/00* | (2006.01) | |
| *G02B 13/18* | (2006.01) | |
| *G02B 13/04* | (2006.01) | |
| *G02B 5/00* | (2006.01) | |

(52) U.S. Cl.
CPC ........... *G02B 9/60* (2013.01); *G02B 13/0015* (2013.01); *A61B 1/00163* (2013.01); *G02B 5/005* (2013.01); *G02B 13/0045* (2013.01); *G02B 13/04* (2013.01); *G02B 13/18* (2013.01); *G02B 23/243* (2013.01)

(58) Field of Classification Search
CPC ...... G02B 13/0045; G02B 9/60; G02B 13/18; G02B 5/005; G02B 13/04; G02B 23/243; G02B 13/0015; A61B 1/00163

USPC .......................... 359/714, 740, 753, 763, 770
See application file for complete search history.

(56) References Cited

U.S. PATENT DOCUMENTS

| | | | | |
|---|---|---|---|---|
| 4,403,837 A | * | 9/1983 | Nakahashi | G02B 9/60 359/740 |
| 6,075,658 A | * | 6/2000 | Nagahara | G02B 13/04 359/740 |
| 6,825,993 B2 | * | 11/2004 | Noda | G02B 13/04 359/680 |
| 7,538,958 B2 | * | 5/2009 | Tang | G02B 13/04 359/770 |
| 7,663,814 B2 | * | 2/2010 | Kitahara | G02B 13/146 359/770 |
| 8,040,618 B2 | * | 10/2011 | Kitahara | G02B 9/62 359/752 |
| 8,570,670 B2 | * | 10/2013 | Kubota | G02B 13/04 359/753 |

(Continued)

FOREIGN PATENT DOCUMENTS

| | | |
|---|---|---|
| JP | H11-249008 A | 9/1999 |
| JP | 5274728 B2 | 8/2013 |
| JP | 5653243 B2 | 1/2015 |

*Primary Examiner* — Evelyn A Lester
(74) *Attorney, Agent, or Firm* — Paratus Law Group, PLLC

(57) ABSTRACT

An imaging optical system includes, in order from an object side, a first lens having negative refractive power, a second lens having positive refractive power, a third lens having positive refractive power, a fourth lens and a fifth lens, with the fourth lens and the fifth lens not cemented, in which a predetermined conditional expressions is satisfied.

17 Claims, 13 Drawing Sheets

(56) References Cited

U.S. PATENT DOCUMENTS

| | | | |
|---|---|---|---|
| 8,743,485 B2* | 6/2014 | Hsieh | G02B 9/60 |
| | | | 359/770 |
| 8,953,258 B1* | 2/2015 | Liao | G02B 3/04 |
| | | | 359/714 |
| 9,013,812 B2* | 4/2015 | Kubota | G02B 13/003 |
| | | | 359/753 |
| 9,927,597 B2* | 3/2018 | Lee | G02B 13/0045 |
| 10,007,105 B2* | 6/2018 | Kamo | G02B 9/60 |
| 10,197,767 B2* | 2/2019 | Lin | G02B 9/60 |
| 2007/0236811 A1* | 10/2007 | Mori | G02B 13/004 |
| | | | 359/770 |
| 2008/0055741 A1* | 3/2008 | Asami | G02B 9/34 |
| | | | 359/738 |
| 2012/0069140 A1* | 3/2012 | Tsai | G02B 9/34 |
| | | | 359/715 |
| 2012/0307382 A1* | 12/2012 | Hsu | G02B 13/0045 |
| | | | 359/770 |
| 2013/0317299 A1 | 11/2013 | Fujii | |
| 2014/0018628 A1 | 1/2014 | Kanazawa et al. | |
| 2014/0029118 A1* | 1/2014 | Yoo | G02B 13/24 |
| | | | 359/715 |
| 2014/0198398 A1 | 7/2014 | Kanazawa et al. | |
| 2014/0368931 A1* | 12/2014 | Noda | G02B 9/62 |
| | | | 359/740 |
| 2015/0092284 A1* | 4/2015 | Liao | G02B 13/0045 |
| | | | 359/714 |
| 2019/0179119 A1* | 6/2019 | Kubota | G02B 13/06 |

* cited by examiner

IMAGING OPTICAL SYSTEM AND IMAGE CAPTURING APPARATUS

CROSS-REFERENCE TO RELATED APPLICATIONS

This application is based on and claims the benefit of priority from Japanese Patent Application No. 2019-034347, filed on Feb. 27, 2019, the entire contents of which are incorporated herein by reference.

BACKGROUND OF THE INVENTION

Technical Field

The present invention relates to an imaging optical system and an image capturing apparatus including the same.

Related Art

Imaging optical systems are often required to have a wider angle of view and a smaller size, while maintaining optical performances such as high resolution, for the sake of usability and manufacturing cost. In particular, a medical image capturing apparatus, such as endoscopes, are strongly demanded to be what is known as minimally invasive, so that a damage on a patient's body can be made small. In this context, the apparatus is strongly demanded to be downsized with an instrument inserted into an affected area made small in an attempt to reduce tissues to be damaged. In the present specification, the downsizing of the imaging optical system means reducing the diameter of a lens that is a component, and shortening the total optical length of the imaging optical system corresponding to a distance between an object side surface and an imaging position.

In recent years, due to the advancement and development of image processing software for image capturing apparatuses, an image with desired accuracy can be obtained by performing correction by image processing even if the imaging optical system is somewhat distorted. Thus, imaging optical systems and image capturing apparatuses are now demanded to be designed while relatively focusing on achieving wider angle of view and a smaller size, without compromising the imaging performance.

One conventional technique related to such an imaging optical system proposes an optical system, for an endoscope, with a lens configuration including a front lens group and a rear lens group arranged respectively on front and rear sides of a stop. The front lens group includes negative and positive lenses in this order from the object side. The rear lens group that is more on the image side than the stop includes a positive lens and a cemented lens (negative/positive). The system is based on conditional expressions related to the focal length of the entire system, an air equivalent distance between an image plane and an exit pupil, and a focal length of the rear group (see, for example, JP 5653243 B2).

In JP 5653243 B2, there is problems that the power of the rear lens group is too low, and that the total optical length of the imaging optical system is long.

An imaging lens proposed as another prior art (see, for example, JP 11-249008 A) of the imaging optical system described above includes a front lens group, a stop, and a rear lens group. The front lens group consists of a plano-concave lens/bi-concave lens and a bi-convex lens. The rear lens group has positive refractive power. Focusing is performed with only the rear lens group moved. With this configuration, optical performance that is equivalent to or higher than conventional configuration can be achieved, even when five lenses or less is used and when no aspherical lens is used.

An example of the imaging lens according to JP 11-249008 A has a lens configuration including, in order from the object side, a front lens group, a stop, and a rear lens group. The front lens group includes a negative lens and a positive lens. The rear lens group is more on the image side than the stop and has positive refractive power (positive/negative/positive). However, due to the rear lens group having excessively strong power, the half angle of view is small, making it difficult to widen the angle of view.

An objective optical system for an endoscope according to still another prior art of the imaging optical system described above includes, in order from the object side, a first lens consisting of a single negative lens, a second lens consisting of a single positive lens, a brightness stop, a third lens consisting of a single positive lens, and a fourth lens including a positive cemented lens. The first lens has a flat object side surface. The second lens has a flat image side surface. The third lens has a meniscus shape with a convex side facing the image side. The system satisfies a predetermined conditional expression (see, for example, JP 5274728 B2).

In the objective optical system for an endoscope according to JP 5274728 B2, a power configuration of a lens according to an example includes negative, positive, positive, positive, and negative lenses arranged in this order from the object side, with the positive fourth lens and the negative fifth lens cemented. The objective optical system for an endoscope features the positive fourth lens and the negative fifth lens cemented to achieving an object of the invention which is "enabling curvature of field and coma aberration to be corrected at once, . . . with a relatively small angle" (paragraph [0008]). Thus, JP 5274728 B2 has no teaching or indication contributing to the present invention an object of which is to increase the angle of view.

An object of the present invention is to provide an imaging optical system and an image capturing apparatus that can overcome the above-described problems of the conventional imaging optical system and the image capturing apparatus, and achieve a wide angle of view as well as downsizing, that is, a smaller aperture and a shorter total optical length, while maintaining the excellent imaging performance with aberration highly accurately corrected.

SUMMARY OF THE INVENTION

An imaging optical system according to the present invention includes, in order from an object side, a first lens G1 having negative refractive power, a second lens G2 having positive refractive power, a third lens G3 having positive refractive power, a fourth lens G4 and a fifth lens G5, with the fourth lens G4 and the fifth lens G5 not cemented, and satisfies following conditional expressions:

$$1.10 \leq f2/f \leq 1.60, \text{ and} \quad (1)$$

$$1.47 \leq f3/f \leq 1.90, \quad (2)$$

where
f2 is a focal length of G2,
f3 is a focal length of G3, and
f is a focal length of the imaging optical system.

An image capturing apparatus according to the present invention includes the imaging optical system and an image sensor that is provided on an imaging plane of the imaging optical system and converts an optical image formed by the imaging optical system into an electric signal.

The present invention can provide an imaging optical system and an image capturing apparatus that can achieve a wide angle of view as well as downsizing, that is, a smaller aperture and a shorter total optical length, while maintaining the excellent imaging performance with aberration highly accurately corrected.

DESCRIPTION OF THE EMBODIMENTS

Figure 1:
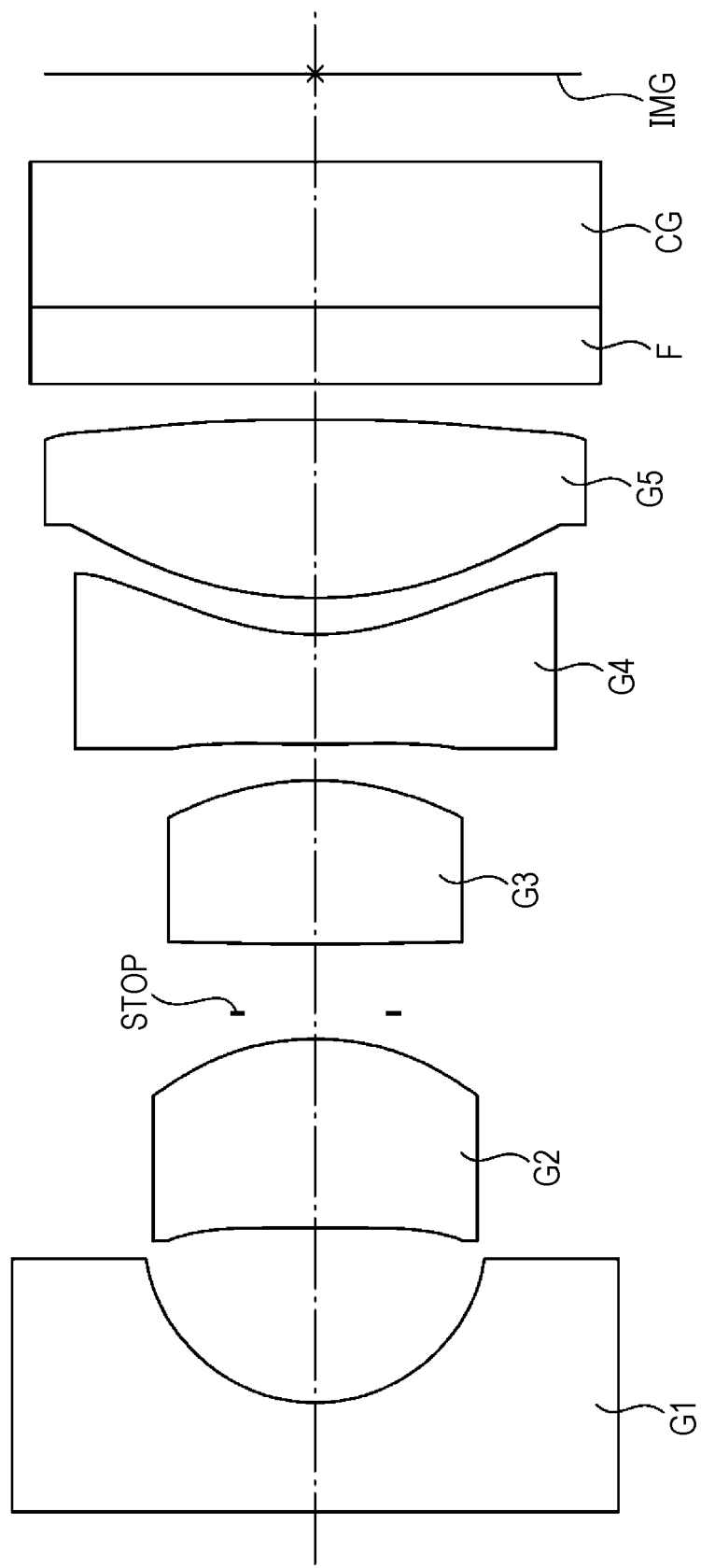
FIG. 1 illustrates an optical configuration of an imaging optical system according to a first example of the present invention.
Figure 2:
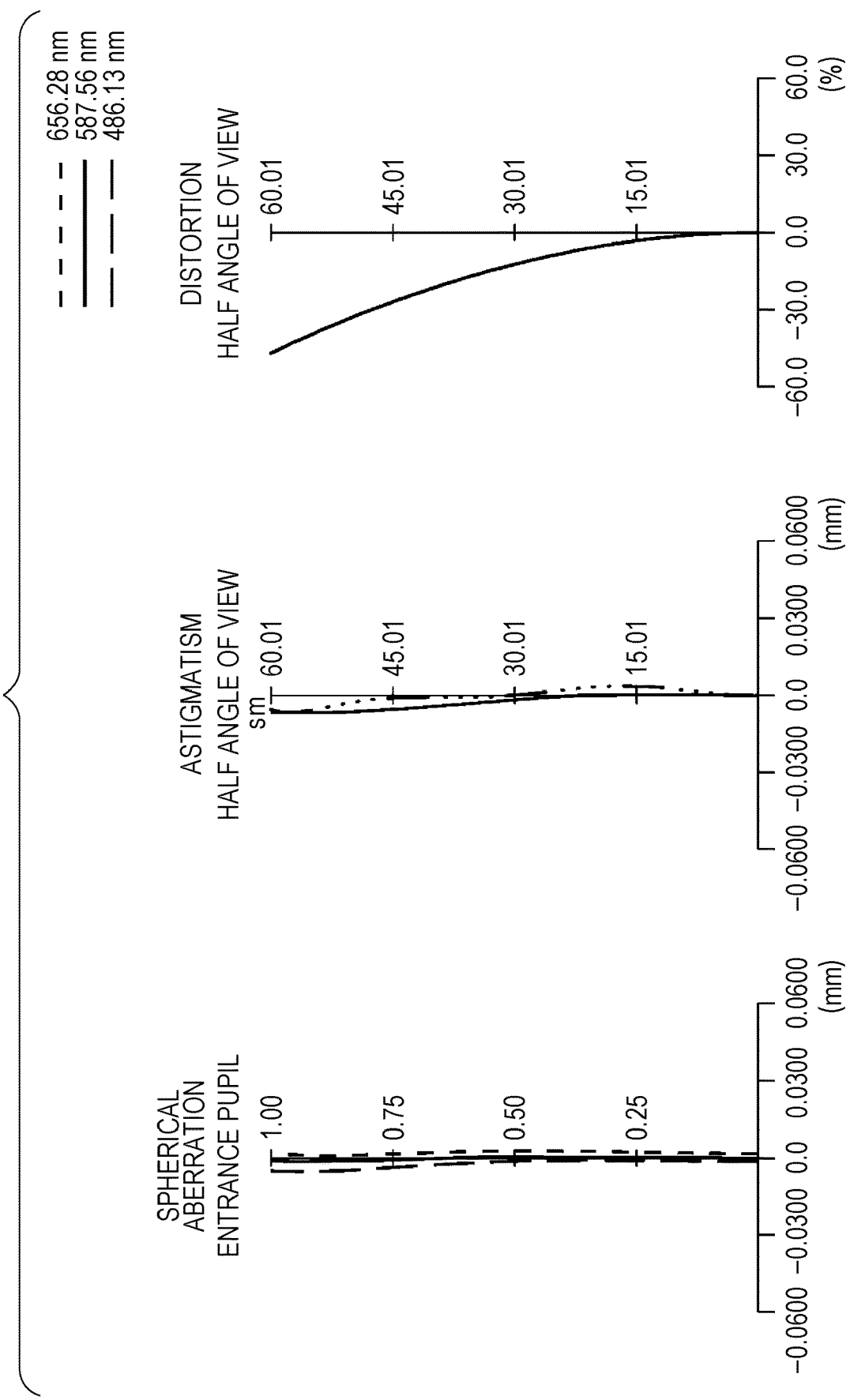
FIG. 2 is a diagram illustrating aberration of the imaging optical system according to the first example of the present invention.

An imaging optical system according to the present invention preferably satisfies at least one of the following conditional expressions or configurational conditions. Hereinafter, preferred embodiments of the present invention will be described.

An imaging optical system according to the present invention includes, in order from an object side, a first lens G1 having negative refractive power, a second lens G2 having positive refractive power, a third lens G3 having positive refractive power, a fourth lens G4, and a fifth lens G5. The fourth lens G4 and the fifth lens G5 are not cemented.

The configuration of the imaging optical system according to the present invention features the first lens G1 having negative refractive power provided, and this is advantageous to achieve a small diameter of the first lens on the object side and a wide angle of view. The arrangement of the second lens G2 having the positive refractive power enables the total optical length of the imaging optical system to be short and distortion and astigmatism occurring due to the first lens G1 to be effectively corrected, and thus is advantageous to achieve the imaging optical system with a wider angle of view. The arrangement of the third lens G3 having positive refractive power is advantageous to correct large spherical aberration occurring due to the first lens G1.

The fourth lens G4 and the lens arranged more on the image side than the fourth lens G4 involve passage of a principal ray of a light flux, reaching an area around the field of view, through positions of the lenses higher than the optical axis, resulting in a small chief ray angle (CRA, an incident angle of the chief ray on the sensor relative to the optical axis). The lenses are further advantageous to correct the curvature of field and distortion.

The fourth lens G4 and the fifth lens G5 not cemented and having no limit condition for cementing are advantageous to correct the distortion and astigmatism in a peripheral angle of view, and can achieve a wider angle of view.

The imaging optical system according to the present invention preferably satisfies a conditional expression (1):

$$1.10 \leq f2/f \leq 1.60, \quad (1)$$

where
f2 is a focal length of the second lens G2, and
f is a focal length of the imaging optical system.

The conditional expression (1) defines the ratio between the focal length of the second lens G2 and the focal length of the imaging optical system. A value satisfying the conditional expression (1) enables distortion and astigmatism occurring due to the first lens G1 to be easily corrected and a wide angle of view to be achieved, while achieving a short total optical length of the imaging optical system.

A value exceeding the upper limit of the conditional expression (1) results in insufficient aberration correction for distortion and astigmatism.

A value below the lower limit of the conditional expression (1) results in excessive aberration correction for distortion and astigmatism.

The upper limit of the conditional expression (1) is more preferably 1.50, and is even more preferably 1.40.

The lower limit of the conditional expression (1) is more preferably 1.15, and is even more preferably 1.17.

Preferably, the imaging optical system according to the present invention satisfies a conditional expression (2):

$$1.47 \leq f3/f \leq 1.90, \quad (2)$$

where
f3 is a focal length of the third lens G3.

The conditional expression (2) defines the ratio between the focal length of the third lens G3 and the focal length of the imaging optical system. A value satisfying the conditional expression (2) enables aberration such as spherical aberration that occurs due to the first lens G1 to be cancelled, with a strong positive lens arranged for the third lens G3.

A value exceeding the upper limit of the conditional expression (2) results in insufficient aberration correction.

A value below the lower limit of the conditional expression (2) results in excessive aberration correction.

The upper limit of the conditional expression (2) is more preferably 1.85, and is even more preferably 1.75.

The lower limit of the conditional expression (2) is more preferably 1.50, and is even more preferably 1.55.

Preferably, the imaging optical system according to the present invention satisfies a conditional expression (3):

$$45.0 \leq W \leq 80.0, \quad (3)$$

where

W is a half angle of view (°).

The conditional expression (3) defines a half angle of view of the imaging optical system as a condition for effectively implementing the aberration correction based on at least one of the conditional expression (1) and the conditional expression (2). A value satisfying the conditional expression (3) as well as at least one of the conditional expression (1) and the conditional expression (2) enables an imaging optical system with higher performance, smaller size, and a wider angle of view to be implemented.

The upper limit of the conditional expression (3) is more preferably 75.0, and is even more preferably 70.0.

The lower limit of the conditional expression (3) is more preferably 50.0, and is even more preferably 55.0.

Preferably, the imaging optical system according to the present invention satisfies a conditional expression (4):

$$0.50 \le f12/f \le 7.00, \qquad (4)$$

where f12 is a combined focal length of the first lens G1 and the second lens G2.

The conditional expression (4) defines the ratio between the combined focal length of the first lens G1 and the second lens G2 and the focal length of the imaging optical system. A value satisfying the conditional expression (4) enables an imaging optical system featuring a shorter total length as well as the reduction of the diameter and the widening of the angle of view achieved in a balanced manner to be provided.

A value exceeding the upper limit of the conditional expression (4) enables the angle of view to be increased and the diameter to be reduced, but also results in a larger total length.

A value below the lower limit of the conditional expression (4) enables the reduction of the total length, but renders the reduction of the diameter and the increase in the angle of view difficult.

The upper limit of the conditional expression (4) is more preferably 6.00, and is even more preferably 5.50.

The lower limit of the conditional expression (4) is more preferably 1.00, and is even more preferably 1.40.

It is preferable that the imaging optical system according to the present invention satisfy a conditional expression (5):

$$0.10 \le D12/f \le 1.00, \qquad (5)$$

where

D12 is a distance between the first lens G1 and the second lens G2.

The conditional expression (5) defines the ratio of the distance between the first lens G1 and the second lens G2 to the focal length of the imaging optical system. A value satisfying the conditional expression (5) enables downsizing and a wider angle of view to be achieved in a balanced manner.

A value exceeding the upper limit of the conditional expression (5) enables the angle of view to be increased, but also results in a large diameter.

A value below the lower limit of the conditional expression (5) enables the reduction of the diameter, but renders the increase in the angle of view difficult.

The upper limit of the conditional expression (5) is more preferably 0.70, and is even more preferably 0.65.

The lower limit of the conditional expression (5) is more preferably 0.20, and is even more preferably 0.25.

It is preferable that the imaging optical system according to the present invention satisfy a conditional expression (6):

$$47.0 \le v2 \le 60.0, \qquad (6)$$

where v2 is Abbe number for d-line of the second lens G2.

The conditional expression (6) defines the Abbe number for d-line of the second lens G2. A value satisfying the conditional expression (6) enables axial chromatic aberration to be easily corrected.

A value exceeding the upper limit of the conditional expression (6) corresponds to a glass material having a small refractive index requiring a high curvature of the lens, resulting in more aberration occurring on the lens surface. Furthermore, there are limited options of the glass materials for the second lens G2, and thus a freedom of selection of the optical constant is limited.

A values below the lower limit of the conditional expression (6) renders the correction of axial chromatic aberration difficult.

The upper limit of the conditional expression (6) is more preferably 58.0, and is even more preferably 56.5.

The lower limit of the conditional expression (6) is more preferably 48.0, and is even more preferably 49.0.

It is preferable that the imaging optical system according to the present invention satisfy a conditional expression (7):

$$3.30 \le OAL \le 4.35, \qquad (7)$$

where

OAL is a total optical length (mm) of the imaging optical system. This OAL indicating the actual dimension of the imaging optical system including no air equivalent length of the CG in a case of a lens with the CG inserted. The CG is a cover glass, a filter, a prism, or the like with no refractive power.

The conditional expression (7) defines the total optical length of the imaging optical system as a condition for obtaining an imaging optical system with a wide angle of view and a smaller diameter achieved in a balanced manner.

A value exceeding the upper limit of the conditional expression (7) results in a problem that it becomes difficult to provide a configuration suitable for an imaging optical system for endoscopes, in-vehicle devices, and surveillance devices.

A value below the lower limit of the conditional expression (7) results in a problem that it becomes difficult to achieve aberration correction.

The upper limit of the conditional expression (7) is more preferably 4.33, and is even more preferably 4.20.

The lower limit of the conditional expression (7) is more preferably 3.40, and is even more preferably 3.50.

It is preferable that the imaging optical system according to the present invention satisfy a conditional expression (8):

$$0.08 \le D45/f \le 0.40, \qquad (8)$$

where

D45 is a distance between the fourth lens G4 and the fifth lens G5.

The conditional expression (8) defines the ratio of the distance between the fourth lens G4 and the fifth lens G5 to the focal length of the imaging optical system. A value satisfying the conditional expression (8) enables aberration due to curvature of field and distortion to be easily corrected.

A value exceeding the upper limit of the conditional expression (8) results in difficulty in correcting the aberration due to curvature of field aberration and the distortion, as well as a long total length and a difficulty in reduction of the diameter.

A value below the lower limit of the conditional expression (8) renders correction of aberration due to curvature of field and distortion difficult.

The upper limit of the conditional expression (8) is more preferably 0.37, and is even more preferably 0.30.

The lower limit of the conditional expression (8) is more preferably 0.10, and is even more preferably 0.11.

It is preferable that the imaging optical system according to the present invention satisfy a conditional expression (9):

$$-1.30 \leq f1/f \leq -0.60, \quad (9)$$

where f1 is a focal length of the first lens G1.

The conditional expression (9) defines the ratio between the focal length of the first lens G1 and the focal length of the imaging optical system. A value satisfying the conditional expression (9) enables the diameter of the front lens, that is, the lens on the object side to be reduced, and is advantageous to increase the angle of view.

A value exceeding the upper limit of the conditional expression (9) renders correction of aberration occurring due to the first lens G1 difficult.

A value below the lower limit of the conditional expression (9) results in a larger diameter of the first lens G1, and renders the increase in the angle of view difficult.

The upper limit of the conditional expression (9) is more preferably −0.70, and is even more preferably −0.75.

The lower limit of the conditional expression (9) is more preferably −1.22, and is even more preferably −1.21.

It is preferable that the imaging optical system according to the present invention satisfy a conditional expression (10):

$$0.80 \leq |f4|/f \leq 3.60, \quad (10)$$

where f4 is a focal length of the fourth lens G4.

The conditional expression (10) defines the ratio between the focal length of the fourth lens G4 and the focal length of the imaging optical system. A value satisfying the conditional expression (10) is effective for correcting the curvature of field and distortion, for the fourth lens through which a principal ray having a peripheral image height passes a position relatively high with respect to the optical axis.

A value exceeding the upper limit of the conditional expression (10) renders correction of the curvature of field and distortion.

A value below the lower limit of the conditional expression (10) renders correction of aberration occurring due to the fourth lens G4 difficult.

The upper limit of the conditional expression (10) is more preferably 3.40, and is even more preferably 3.30.

The lower limit of the conditional expression (10) is more preferably 1.00, and is even more preferably 1.20.

It is preferable that the imaging optical system according to the present invention satisfy a conditional expression (11):

$$1.70 \leq |f5|/f \leq 450.00, \quad (11)$$

where f5 is a focal length of the fifth lens G5.

The conditional expression (11) defines the ratio between the an absolute value of the focal length of the fifth lens G5 and the focal length of the imaging optical system. A value satisfying the conditional expression (11) results in the fifth lens G5 through which a principal ray having a peripheral image height passes a position higher than the optical axis, and thus is advantageous in controlling increase/decrease in CRA.

A value exceeding the upper limit of the conditional expression (11) renders the increase or decrease of CRA difficult to control.

A value below the lower limit of the conditional expression (11) results in a problem that new aberration which is difficult to correct is generated by the fifth lens G5.

The upper limit of the conditional expression (11) is more preferably 420, and is even more preferably 410.

The lower limit of the conditional expression (11) is more preferably 1.80, and is even more preferably 1.90.

It is preferable that the imaging optical system according to the present invention satisfy a conditional expression (12):

$$0.35 \leq RG1R2/f \leq 0.80, \quad (12)$$

where

RG1R2 is a radius of curvature of an image side surface of the first lens G1.

The conditional expression (12) defines a ratio between the radius of curvature of the image side surface of the first lens G1 and the focal length of the imaging optical system. A value satisfying the conditional expression (12) enables the curvature of field occurring on the object side surface of the first lens G1 to be corrected.

A value exceeding the upper limit of the conditional expression (12) renders aberration occurring on the object side surface of the first lens G1 difficult to correct.

A value below the lower limit of the conditional expression (12) results in an excessively small radius of curvature of the image side surface of the first lens G1 which leads to occurrence of aberration, and thus is disadvantageous to achieve higher performance.

The upper limit of the conditional expression (12) is more preferably 0.75, and is even more preferably 0.73.

The lower limit of the conditional expression (12) is more preferably 0.38, and is even more preferably 0.42.

It is preferable that the imaging optical system according to the present invention satisfy a conditional expression (13):

$$-1.20 \leq RG2R2/f \leq -0.40, \quad (13)$$

where

RG2R2 is a radius of curvature of an image side surface of the second lens G2.

The conditional expression (13) defines a ratio between the radius of curvature of the image side surface of the second lens G2 and the focal length of the imaging optical system. A value satisfying the conditional expression (13) enables the axial chromatic aberration and spherical aberration occurring on the object side surface of the second lens G2 to be efficiently corrected.

A value exceeding the upper limit of the conditional expression (13) results in an excessively small radius of curvature of the image side surface of the second lens G2 which leads to occurrence of aberration, and thus is disadvantageous to achieve higher performance.

A value below the lower limit of the conditional expression (13) renders axial chromatic aberration and spherical aberration occurring on the object side surface of the second lens G2 difficult to correct.

The upper limit of the conditional expression (13) is more preferably −0.50, and is even more preferably −0.53.

The lower limit of the conditional expression (13) is more preferably −1.00, and is even more preferably −0.75.

It is preferable that the imaging optical system according to the present invention satisfy a conditional expression (14):

$$-1.40 \leq RG3R2/f \leq -0.50, \quad (14)$$

where

RG3R2 is a radius of curvature of an image side surface of the third lens G3.

The conditional expression (14) defines a ratio between the radius of curvature of the image side surface of the third lens G3 and the focal length of the imaging optical system. A value satisfying the conditional expression (14) enables spherical aberration occurring on an object side surface of the third lens G3 to be corrected.

A value exceeding the upper limit of the conditional expression (14) results in an excessively small radius of curvature of the image side surface of the third lens G3 which leads to occurrence of aberration, and thus is disadvantageous to achieve higher performance.

A value below the lower limit of the conditional expression (14) renders spherical aberration occurring on the object side surface of the third lens G3 difficult to correct.

The upper limit of the conditional expression (14) is more preferably −0.52, and is even more preferably −0.70.

The lower limit of the conditional expression (14) is more preferably −1.30, and is even more preferably −1.00.

The imaging optical system according to the present invention is a single focus lens, and is usable not only as an image forming lens having a focusing mechanism, but is also usable as a fixed single focus lens having no focusing mechanism for the sake of simplification of the mechanism of the imaging lens, downsizing, and reduction in diameter.

The aperture stop of the imaging optical system according to the present invention is preferably disposed at any position between the first lens G1 and the fourth lens G4 for the sake of downsizing of the first lens G1. In particular, the aperture stop disposed at any position between the first lens G1 and the third lens G3 is more preferable in terms of reduction of the diameter of the first lens G1. Furthermore, the aperture stop disposed between the second lens G2 and the third lens G3 is advantageous to downsize the first lens G1, and of aberration correction for a lower ray farther from the optical axis than the principal ray of the peripheral ray is. Furthermore, the aperture stop disposed between the first lens G1 and the second lens G2 enables further reduction of the diameter of the first lens G1.

Furthermore, the imaging optical system of the present invention can achieve a smaller diameter and a wider angle of view in a balanced manner when the following conditional expression (15) is satisfied:

$$3.80 \leq OAL/f \leq 5.20, \quad (15)$$

where

OAL is the total optical length of the imaging optical system, and f is the focal length of imaging optical system.

In the imaging optical system according to the present invention, it is preferable that the first lens G1 and the second lens G2 are not cemented. With the lenses not cemented, aberration correction can be favorably implemented on the object side surface of the first lens G1 and on the image side surface of the second lens G2, while optimizing the power, required for the first lens G1 and the second lens G2, on the object side surface of the first lens G1 and on the image side surface of the second lens G2, without any limitation due to the shape of the surfaces to be the cemented surfaces. Thus, even higher performance can be achieved.

In the imaging optical system according to the present invention, it is preferable that the second lens G2 and the third lens G3 are not cemented. With the lenses not cemented, aberration correction can be favorably implemented on the object side surface of the second lens G2 and on the image side surface of the third lens G3, while optimizing the power, required for the second lens G2 and the third lens G3, on the object side surface of the second lens G2 and on the image side surface of the third lens G3, without any limitation due to the shape of the surfaces to be the cemented surfaces. Thus, even higher performance can be achieved.

In the imaging optical system according to the present invention, it is preferable that the third lens G3 and the fourth lens G4 are not cemented. Due to the principal ray having the peripheral image height passes through the third lens G3 and the fourth lens G4 at positions that are higher than that in the case of the second lens G2, relative to the optical axis, and providing the plurality of planes comprised of at minimum four planes or more, the curvature of field, distortion, and the like at an intermediate image height can be favorably corrected. Thus, even higher performance can be achieved.

The imaging optical system according to the present invention can also be suitably used as an objective lens for an endoscope, an objective lens for a surveillance device, a lens for an in-vehicle device, and the like, and can further be used as a pan focus lens utilizing a large depth of field.

An image capturing apparatus according to the present invention includes the imaging optical system described above and an image sensor that is provided on an image plane side of the imaging optical system and converts an optical image formed by the imaging optical system into an electric signal.

EXAMPLES

The imaging optical system according to the present invention and the image capturing apparatus including the same will be described below based on numerical examples and the attached drawings.

A numerical example to which a specific numerical value of the imaging optical system according to the present invention is applied will be described.

Note that in the specification table, "focal length" represents the focal length of the entire imaging optical system, F number represents brightness of lens, "half angle of view" represents the half angle of view of the field of view, "lens total length" represents a distance between a first surface of the imaging optical system on the object side and the imaging position and thus represents an entire optical length, and BF (air equivalent) represents air equivalent back focus. Note that f1, f2, f3, f4, f5 and f12 represent focal lengths of the first lens G1, the second lens G2, the third lens G3, the fourth lens G4, the fifth lens G5, and a combination of the first lens G1 and the second lens G2, respectively.

Note that in surface data, No. represents the surface number, r represents the radius of curvature, d represents the lens thickness or distance between lenses, nd represents the refractive index for d-line, and vd represents the Abbe number for d-line. Note that STOP represents an aperture stop, and ASPH represents an aspherical surface. In the surface data, the thickness of a plane-parallel plate such as a filter or a cover glass is provided as a value with non-air equivalent refractive index of the member.

The aspherical surface is defined by the following equation:

$$z = ch^2/[1+(1-(1+k)c^2h^2)^{1/2}] + A4h^4 + A6h^6 + A8h^8 + A10h^{10} \ldots,$$

where c represents curvature (1/r), h represents a height from the optical axis, k represents a conical coefficient, and A4, A6, A8, A10 . . . represent aspherical surface coefficients of respective orders.

In the longitudinal aberration diagrams (FIGS. 2, 4, 6, 8, 10, 12) of examples, spherical aberration (mm), astigmatism (mm), distortion (%) are illustrated in this order from the left side. In a spherical aberration diagram, the vertical axis represents an entrance pupil, the solid line represents characteristics of d-line (587.56 nm), the broken line represents characteristics of C-line (656.28 nm), and the long broken line represents characteristics of F-line (486.13 nm). In an astigmatism diagram, the vertical axis represents the half angle of view, the solid line represents the characteristics of the sagittal image plane (indicated by s in the figure), and the broken line represents the characteristics of the meridional image plane (indicated by m in the figure). In a distortion aberration diagram, the vertical axis represents a half angle of view of d-line.

First Example

As illustrated in FIG. 1, an imaging optical system according to a first example of the present invention includes, in order from the object side, a first lens G1 having negative refractive power, a second lens G2 having positive refractive power, a third lens G3 having positive refractive power, a negative fourth lens G4, and a positive fifth lens G5, as well as a filter F and a cover glass CG adhered to each other. Note that IMG indicates an imaging plane.

The specification table and the focal lengths of the respective lenses according to the first example are as described below.

(Specification table)

| | |
|---|---|
| Focal length | 0.8142 |
| F number | 4 |
| Half angle of view (°) | 60 |
| Lens total length | 3.952 |
| BF (air equivalent) | 0.7433 |
| (Focal length of each lens) | |
| f1 | −0.851 |
| f2 | 1.302 |
| f3 | 1.330 |
| f4 | −1.205 |
| f5 | 1.960 |
| f12 | 3.061 |

The surface data table of the first example is as follows.

(Surface data table)

| No. | r | d | nd | vd |
|---|---|---|---|---|
| 1 | 0.00000 | 0.300 | 1.5462 | 55.88 |
| 2ASPH | 0.46490 | 0.480 | | |
| 3ASPH | 49.99820 | 0.520 | 1.5462 | 55.88 |
| 4ASPH | −0.71870 | 0.070 | | |
| 5STOP | 0.00000 | 0.190 | | |
| 6ASPH | 8.37790 | 0.450 | 1.5462 | 55.88 |
| 7ASPH | −0.78030 | 0.100 | | |
| 8ASPH | 10.71140 | 0.300 | 1.6689 | 20.37 |
| 9ASPH | 0.74100 | 0.100 | | |
| 10ASPH | 1.17140 | 0.490 | 1.5462 | 55.88 |
| 11ASPH | −10.59340 | 0.100 | | |
| 12 | 0.00000 | 0.210 | 1.5256 | 54.52 |
| 13 | 0.00000 | 0.400 | 1.5187 | 64.20 |
| 14 | 0.00000 | 0.242 | | |

Aspherical surface coefficients according to the first example are as follows.

| No. | K | A4<br>A10 | A6<br>A12 | A8<br>A14 |
|---|---|---|---|---|
| 2 | −1.31962E−02 | 7.05019E−02<br>−7.50683E+01 | −1.69269E+00<br>0.00000E+00 | 1.39612E+01<br>0.00000E+00 |
| 3 | 1.00529E+01 | −8.57177E−01<br>0.00000E+00 | −2.88084E+00<br>0.00000E+00 | −2.03723E+00<br>0.00000E+00 |
| 4 | −6.10576E+00 | −2.27820E+00<br>5.32325E+01 | 5.99361E+00<br>8.23249E+01 | −1.91258E+01<br>−3.00364E+02 |
| 6 | −9.99818E+00 | −7.19552E−02<br>3.09859E+01 | 6.33575E−01<br>−1.55050E+00 | −9.03762E+00<br>1.78529E+01 |
| 7 | −2.16412E+00 | 6.12490E−02<br>1.21665E+01 | −2.68807E+00<br>5.37675E+01 | 2.77270E+00<br>−2.76606E+01 |
| 8 | −2.69812E+00 | −4.03667E−01<br>3.43934E+01 | −3.70148E+00<br>4.73528E+00 | 5.78147E−01<br>−8.09837E+00 |
| 9 | −1.64132E−01 | −5.34666E−01<br>−8.43089E−00 | −3.61681E+00<br>−5.61302E+00 | 1.01256E+01<br>8.73337E−01 |
| 10 | −8.09688E+00 | 7.81561E−01<br>−3.57523E+00 | −1.93868E+00<br>1.26977E+00 | 3.48542E+00<br>−1.33983E−00 |
| 11 | 1.00001E+01 | −3.33463E−01<br>−9.50579E−01 | 4.59576E−01<br>−1.13111E+00 | 9.76147E−01<br>−9.28668E−01 |

Second Example

Figure 3:
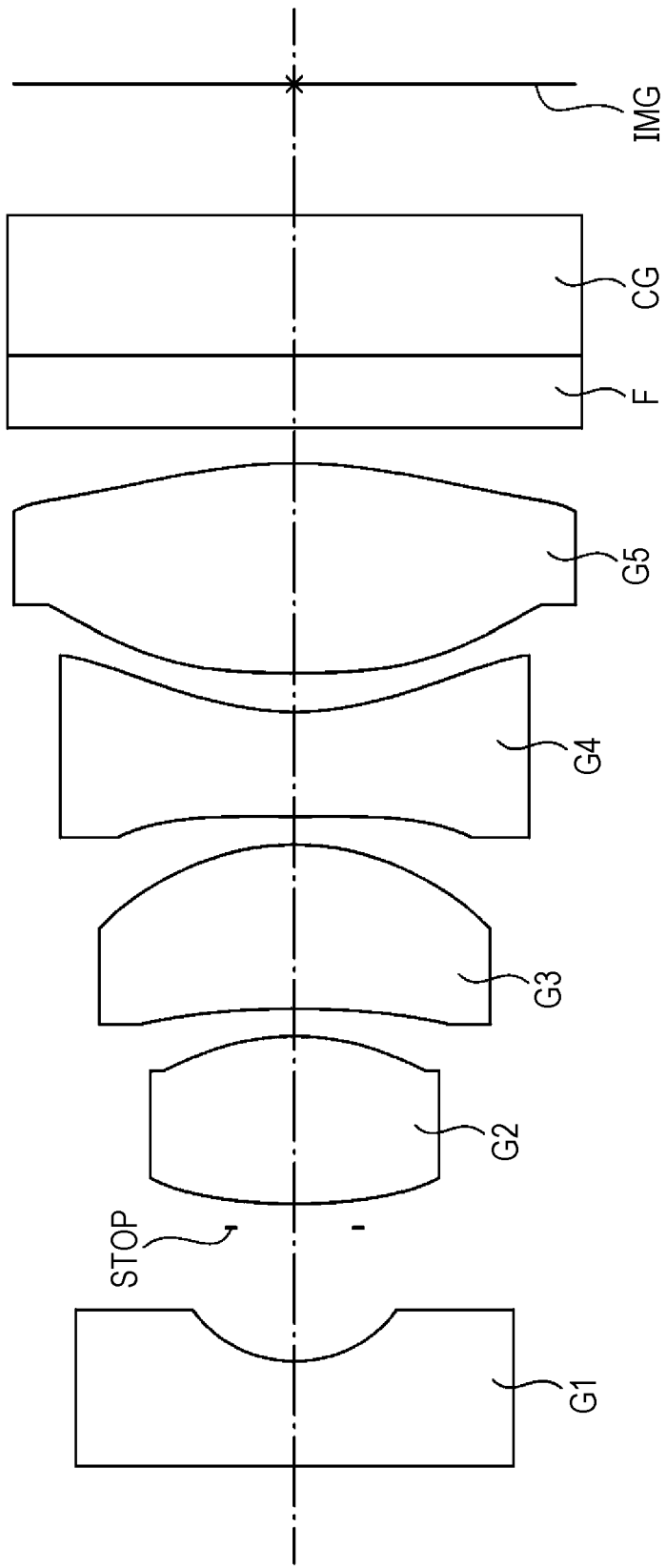
FIG. 3 illustrates an optical configuration of an imaging optical system according to a second example of the present invention.
Figure 4:
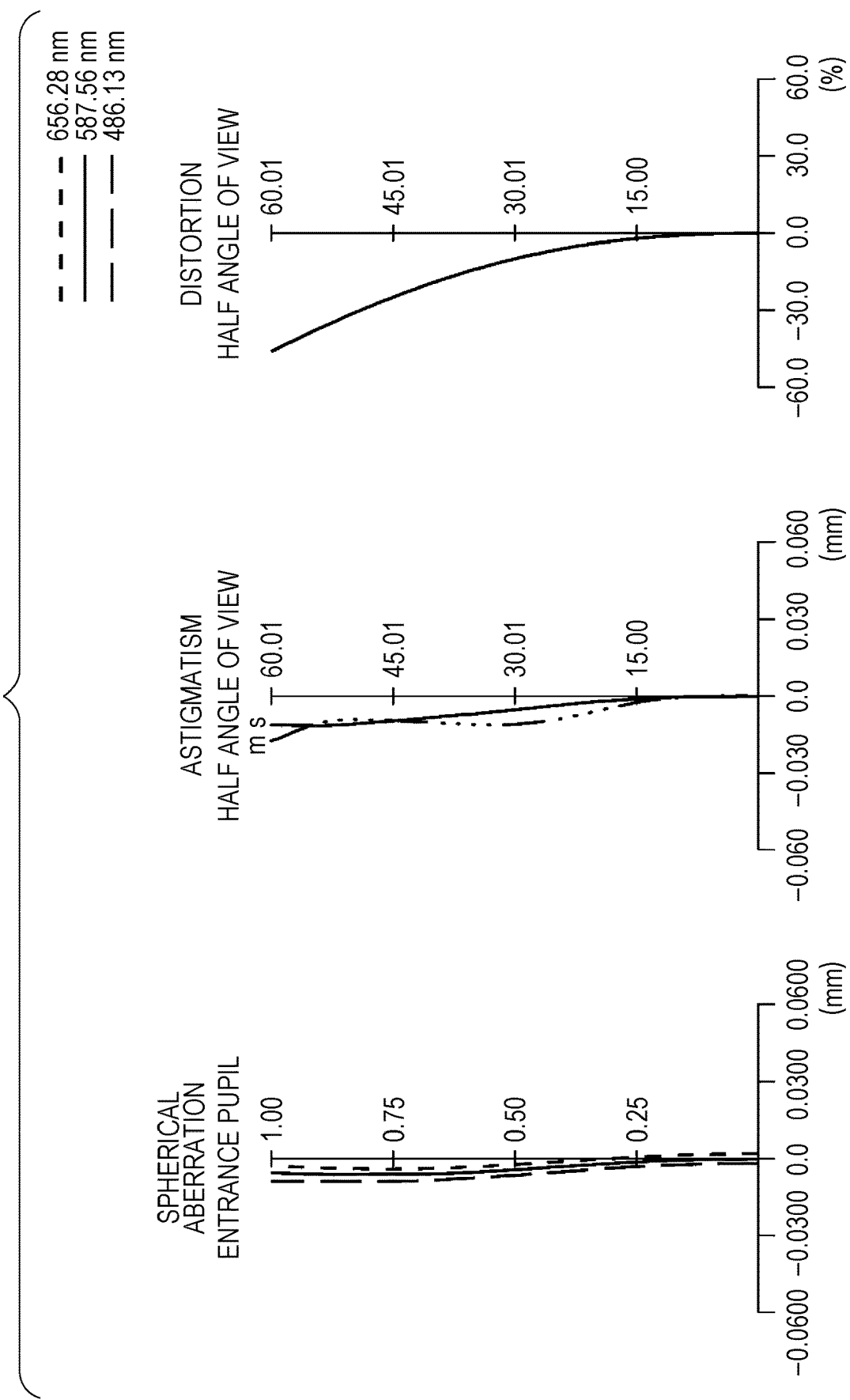
FIG. 4 is a diagram illustrating aberration of the imaging optical system according to the second example of the present invention.

As illustrated in FIG. 3, an imaging optical system according to a second example of the present invention includes, in order from the object side, a first lens G1 having negative refractive power, a second lens G2 having positive refractive power, a third lens G3 having positive refractive power, a negative fourth lens G4, and a positive fifth lens G5, as well as a filter F and a cover glass CG adhered to each other. Note that IMG indicates an imaging plane.

In the second example, the aperture stop of the imaging optical system is disposed between the first lens G1 and the second lens G2. With the aperture stop disposed between the image side surface of the first lens G1 and the second lens G2, the first lens G1 of the imaging optical system can be downsized. This example features the radius of curvature of the image side surface of the first lens G1 being smaller than that in any other examples, and the third lens G3 having weaker refractive power than those in the other examples.

The specification table and the focal lengths of the respective lenses according to the second example are as described below.

| (Specification table) | |
|---|---|
| Focal length | 0.8142 |
| F number | 4 |
| Half angle of view (°) | 60 |
| Lens total length | 3.954 |
| BF (air equivalent) | 0.876054 |
| (Focal length of each lens) | |
| f1 | −0.670 |
| f2 | 0.961 |
| f3 | 1.542 |
| f4 | −1.314 |
| f5 | 1.913 |
| f12 | 1.665 |

The surface data table of the second example is as follows.

| (Surface data table) | | | | |
|---|---|---|---|---|
| No. | r | d | nd | vd |
| 1 | 0.00000 | 0.300 | 1.5462 | 55.88 |
| 2ASPH | 0.36590 | 0.380 | | |
| 3STOP | 0.00000 | 0.070 | | |
| 4ASPH | 1.51340 | 0.480 | 1.5462 | 55.88 |
| 5ASPH | −0.71410 | 0.080 | | |
| 6ASPH | −2.85380 | 0.470 | 1.5462 | 55.88 |
| 7ASPH | −0.68820 | 0.080 | | |
| 8ASPH | 12.74200 | 0.300 | 1.6689 | 20.37 |
| 9ASPH | 0.81470 | 0.110 | | |
| 10ASPH | 3.80970 | 0.600 | 1.5462 | 55.88 |
| 11ASPH | −1.35980 | 0.100 | | |
| 12 | 0.00000 | 0.210 | 1.5187 | 64.20 |
| 13 | 0.00000 | 0.400 | 1.5187 | 64.20 |
| 14 | 0.00000 | 0.374 | | |

Aspherical surface coefficients according to the second example are as follows.

| No. | K | A4<br>A10 | A6<br>A12 | A8<br>A14 |
|---|---|---|---|---|
| 2 | −7.86457E−01 | 1.79066E+00<br>1.80243E+03 | 2.40604E+01<br>0.00000E+00 | −1.26842E+02<br>0.00000E+00 |
| 4 | 7.87472E+00 | −1.03306E−01<br>0.00000E+00 | 1.55882E+00<br>0.00000E+00 | −3.38327E−02<br>0.00000E+00 |
| 5 | −7.10051E+00 | −2.99605E+00<br>3.27769E+02 | 2.28242E+01<br>8.23249E+01 | −1.18998E+02<br>−3.00364E+02 |
| 6 | −1.00000E+01 | −8.77266E−01<br>6.04065E+01 | 6.67134E+00<br>−1.55050E+00 | −3.20461E+01<br>1.78529E+01 |
| 7 | −1.28526E+00 | 1.86807E−02<br>−5.67056E+01 | −2.66024E+00<br>5.37675E+01 | 1.85294E+01<br>−2.76606E+01 |
| 8 | −1.00000E+01 | −1.48982E+00<br>−2.83096E+01 | 1.78866E+00<br>4.73528E+00 | 6.24050E+00<br>−8.09837E+00 |
| 9 | −5.80720E+00 | 7.89327E−02<br>8.56096E+00 | 7.43633E−01<br>−5.61302E+00 | −5.29275E+00<br>8.73337E−01 |
| 10 | 2.11998E+00 | 1.66596E+00<br>−4.22823E+00 | −4.43763E+00<br>1.26977E+00 | 6.26441E+00<br>−1.33983E+00 |
| 11 | 1.11574E−01 | 6.30351E−01<br>3.33072E−01 | −1.15712E+00<br>−1.13111E+00 | 1.50161E+00<br>−9.28668E−01 |

Third Example

Figure 5:
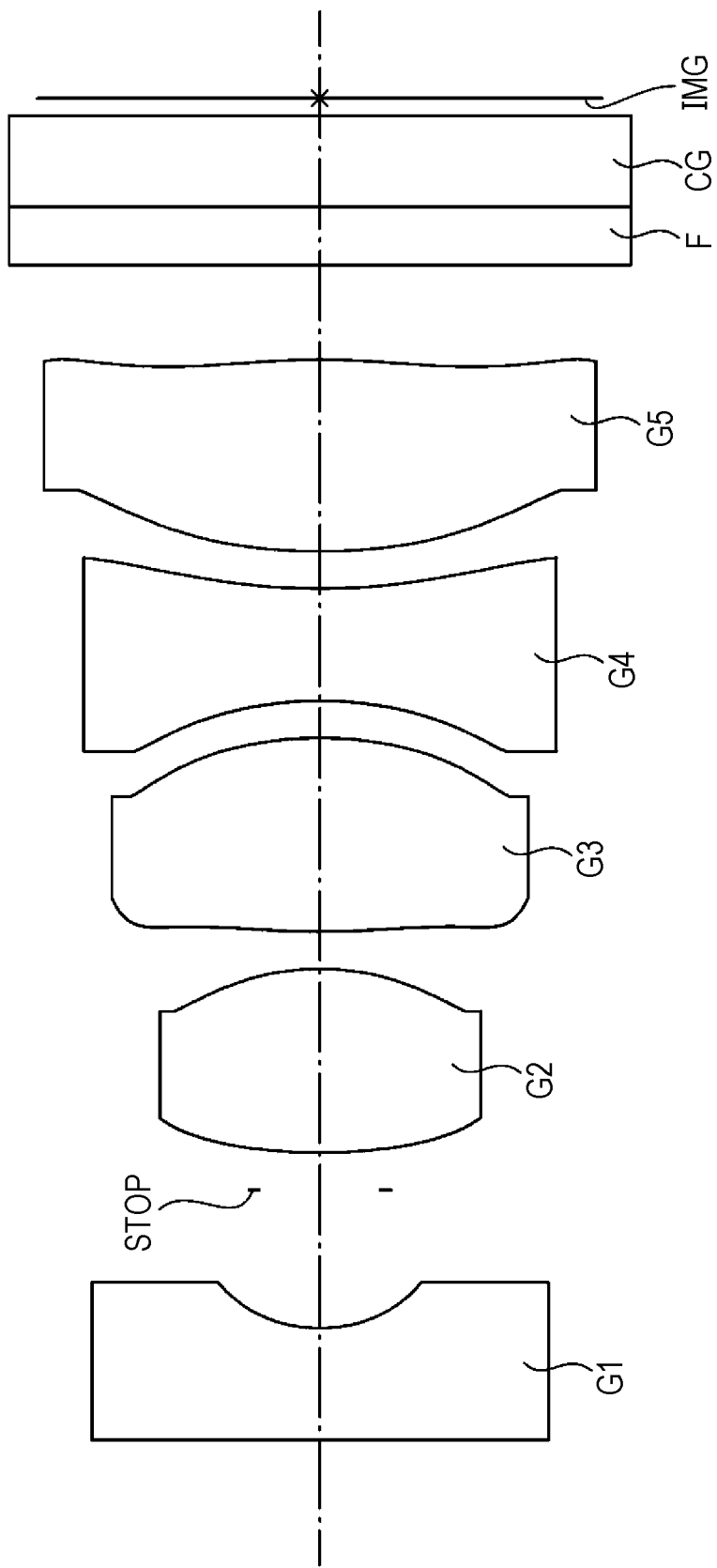
FIG. 5 illustrates an optical configuration of an imaging optical system according to a third example of the present invention.
Figure 6:
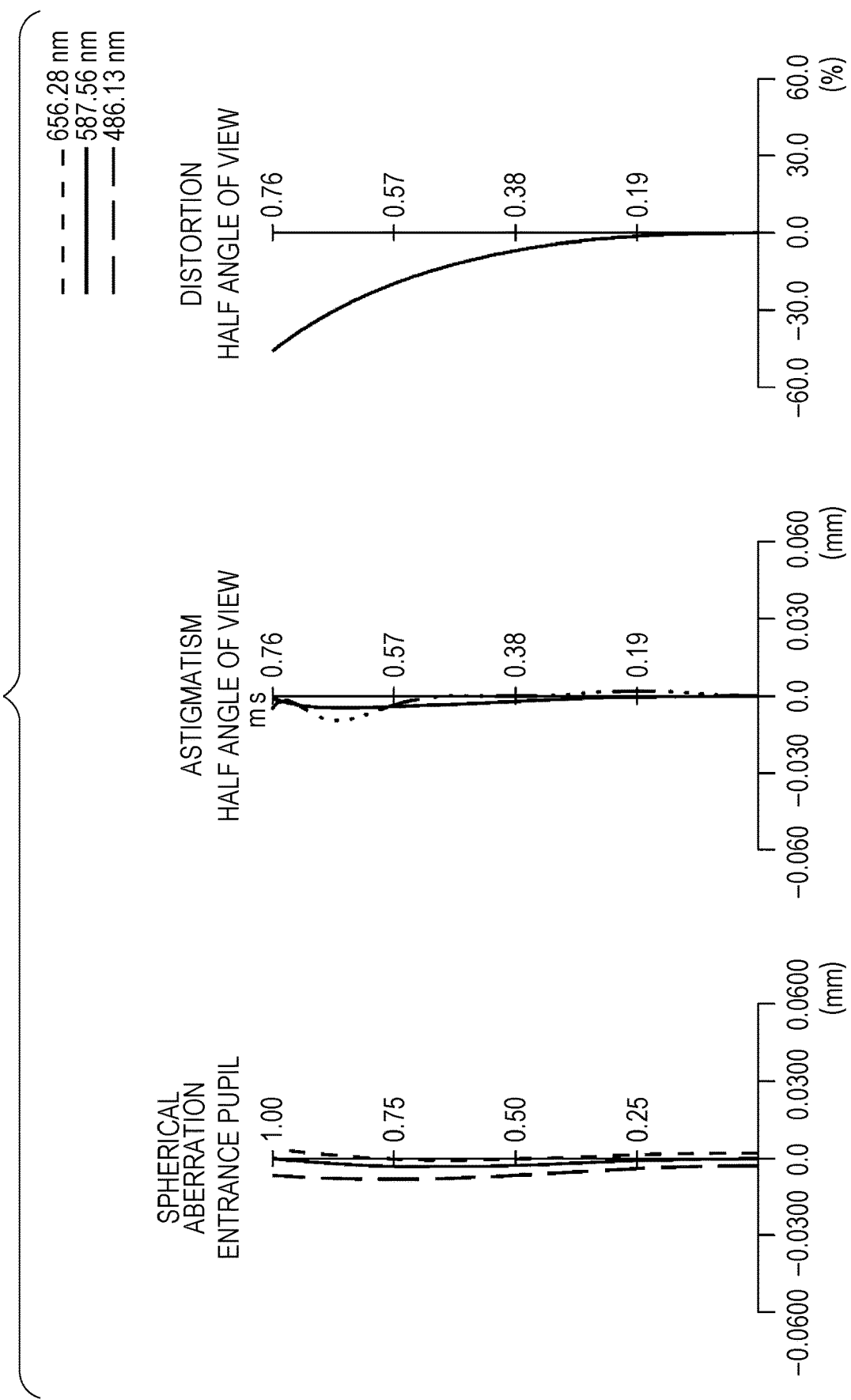
FIG. 6 is a diagram illustrating aberration of the imaging optical system according to the third example of the present invention.

As illustrated in FIG. 5, an imaging optical system according to a third example of the present invention includes, in order from the object side, a first lens G1 having negative refractive power, a second lens G2 having positive refractive power, a third lens G3 having positive refractive power, a negative fourth lens G4, and a positive fifth lens G5, as well as a filter F and a cover glass CG adhered to each other. Note that IMG indicates an imaging plane.

The third example has f12 smaller than that in any other examples with the five-lens configuration, and achieves the shortest total length. This example features the radius of curvature of the image side surface of the third lens G3 being larger than that in any other examples, the radius of curvature of the object side surface of the fourth lens G4 corresponding to a concave surface, and the fourth lens G4 and the fifth lens G5 having stronger refractive power than those in the other examples. The aperture stop of the imaging optical system is provided between the image side surface of the first lens G1 and the second lens G2. With the aperture stop being provided there, the first lens G1 of the imaging optical system is downsized.

The specification table and the focal lengths of the respective lenses according to the third example are as described below.

| (Specification table) | |
|---|---|
| Focal length | 0.8142 |
| F number | 4 |
| Half angle of view (°) | 60 |
| Lens total length | 3.602 |
| BF (air equivalent) | 0.565784 |
| (Focal length of each lens) | |
| f1 | −0.713 |
| f2 | 0.945 |
| f3 | 1.292 |
| f4 | −0.876 |
| f5 | 1.701 |
| f12 | 1.420 |

The surface data table of the third example is as follows.

(Surface data table)

| No. | r | d | nd | vd |
|---|---|---|---|---|
| 1 | 0.00000 | 0.300 | 1.5462 | 55.88 |
| 2ASPH | 0.38920 | 0.370 | | |
| 3STOP | 0.00000 | 0.100 | | |
| 4ASPH | 1.48370 | 0.495 | 1.5462 | 55.88 |
| 5ASPH | −0.69820 | 0.100 | | |
| 6ASPH | 1.92610 | 0.520 | 1.5462 | 55.88 |
| 7ASPH | −1.00690 | 0.100 | | |
| 8ASPH | −0.96050 | 0.300 | 1.6640 | 21.21 |
| 9ASPH | 1.65790 | 0.100 | | |
| 10ASPH | 1.66510 | 0.515 | 1.5462 | 55.88 |
| 11ASPH | −1.87210 | 0.255 | | |
| 12 | 0.00000 | 0.400 | 1.5187 | 64.20 |
| 13 | 0.00000 | 0.047 | | |

Aspherical surface coefficients according to the third example are as follows.

| No. | K | A4<br>A10 | A6<br>A12 | A8<br>A14 |
|---|---|---|---|---|
| 2 | −6.79394E−01 | 2.32669E+00<br>1.32315E+03 | 1.59990E+01<br>−2.27057E−06 | 5.66949E+01<br>−5.33976E−07 |
| 4 | 8.74762E+00 | 2.38817E−02<br>−3.21100E−05 | 8.89577E−01<br>3.08910E−08 | −1.80908E−02<br>2.01131E−08 |
| 5 | −5.31636E+00 | −3.14395E+00<br>3.35365E+02 | 2.20698E+01<br>8.23249E+01 | −1.13909E+02<br>−3.00364E+02 |
| 6 | 5.67994E+00 | −1.98857E+00<br>1.61812E+02 | 1.09891E+01<br>−1.55050E+00 | −6.60630E+01<br>1.78529E+01 |
| 7 | −1.20703E+00 | 1.35220E−01<br>−2.79144E+01 | −7.56267E+00<br>5.37675E−01 | 2.42753E+01<br>−2.76606E+01 |
| 8 | 2.08277E+00 | 7.42867E−01<br>2.31755E+01 | −4.62327E+00<br>4.73528E+00 | 1.30499E+01<br>−8.09837E+00 |
| 9 | −8.54738E−01 | −3.40071E−01<br>1.19509E+01 | 1.81905E+00<br>−5.61302E+00 | −7.86470E+00<br>8.73337E−01 |
| 10 | 8.10053E−01 | 6.84406E−01<br>−3.65396E+00 | −1.99554E+00<br>1.26979E+00 | 3.21889E+00<br>−1.33983E+00 |
| 11 | −1.00000E+01 | 1.06263E+00<br>−9.09714E−01 | −2.04910E+00<br>−1.13114E+00 | 2.40267E+00<br>−9.28668E−01 |

Fourth Example

Figure 7:
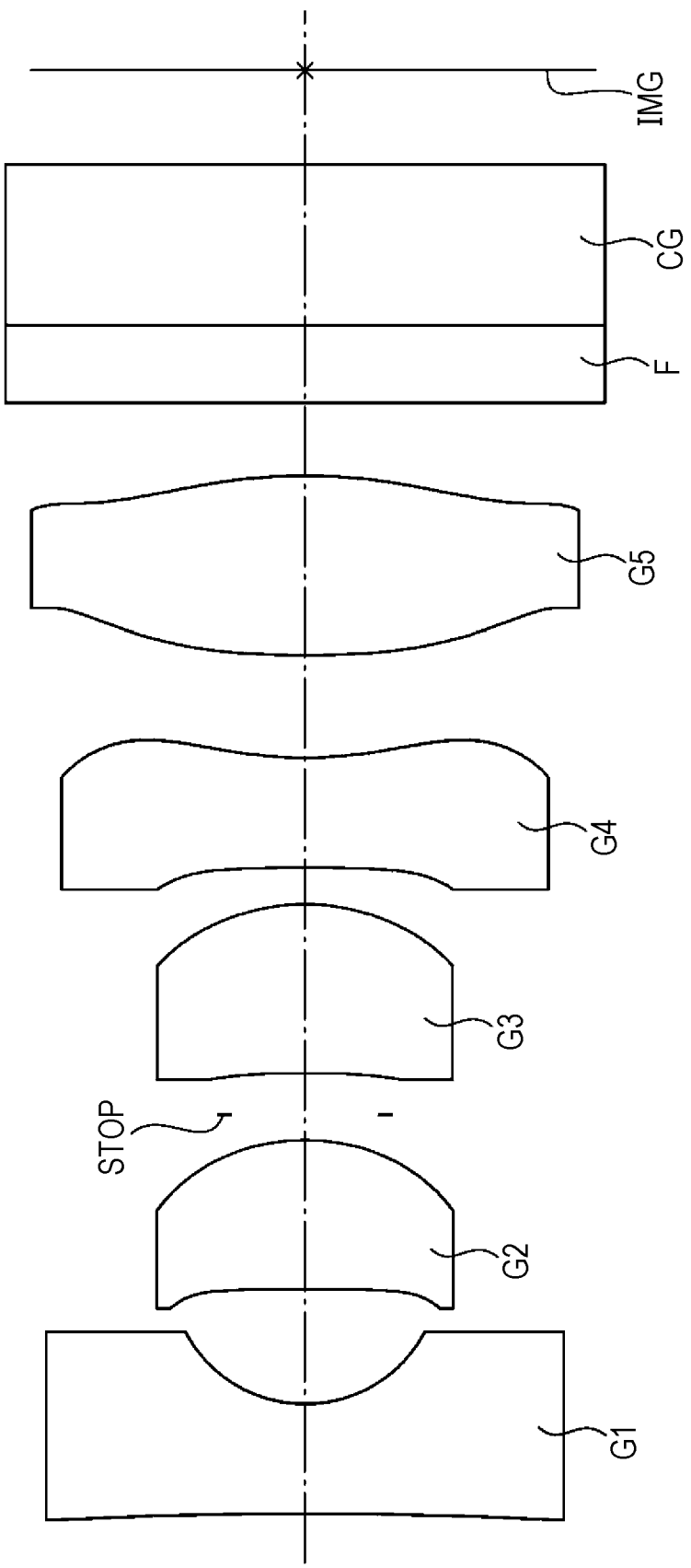
FIG. 7 illustrates an optical configuration of an imaging optical system according to a fourth example of the present invention.
Figure 8:
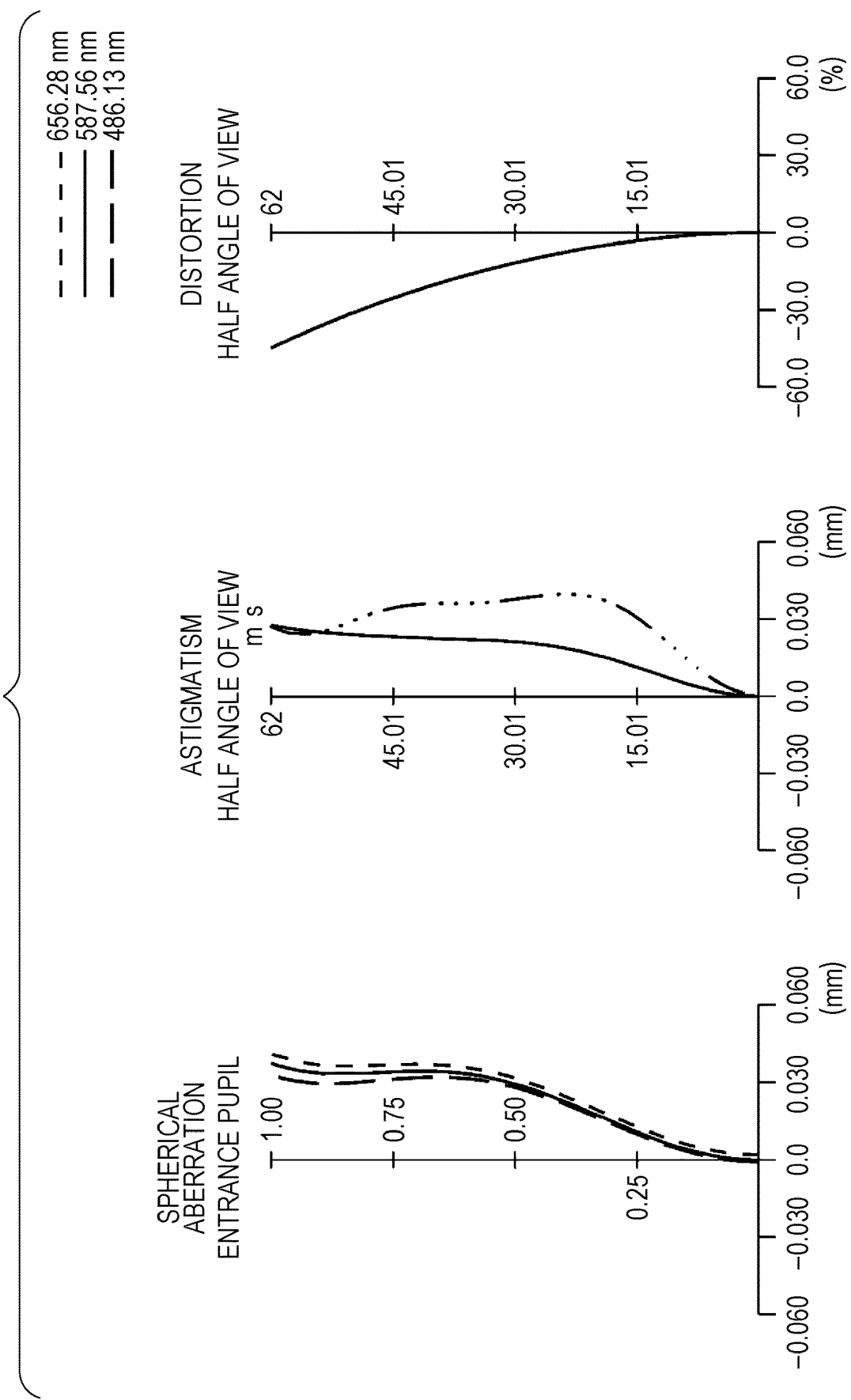
FIG. 8 is a diagram illustrating aberration of the imaging optical system according to the fourth example of the present invention.

As illustrated in FIG. 7, an imaging optical system according to a fourth example of the present invention includes, in order from the object side, a first lens G1 having negative refractive power, a second lens G2 having positive refractive power, a third lens G3 having positive refractive power, a negative fourth lens G4, and a positive fifth lens G5, as well as a filter F and a cover glass CG adhered to each other. Note that IMG indicates an imaging plane.

The fourth example features f12 having the refractive power smaller than that in any other examples with the five-lens configuration.

The specification table and the focal lengths of the respective lenses according to the fourth example are as described below.

(Specification table)

| Focal length | 0.81427 |
|---|---|
| F number | 4 |
| Half angle of view (°) | 60 |
| Lens total length | 3.944 |
| BF (air equivalent) | 0.886821 |

(Focal length of each lens)

| f1 | −0.661 |
|---|---|
| f2 | 1.071 |
| f3 | 1.205 |
| f4 | −1.348 |
| f5 | 1.851 |
| f12 | 4.075 |

The surface data table of the fourth example is as follows.

(Surface data table)

| No. | r | d | nd | vd |
|---|---|---|---|---|
| 1 | −12.90590 | 0.300 | 1.5463 | 55.80 |
| 2ASPH | 0.37460 | 0.313 | | |
| 3ASPH | 50.00000 | 0.407 | 1.5207 | 50.00 |
| 4ASPH | −0.56240 | 0.070 | | |
| 5STOP | 0.00000 | 0.114 | | |
| 6ASPH | −2.45780 | 0.461 | 1.5463 | 55.80 |
| 7ASPH | −0.55370 | 0.100 | | |
| 8ASPH | −7.41800 | 0.300 | 1.6769 | 20.00 |
| 9ASPH | 1.05690 | 0.280 | | |
| 10ASPH | 2.80420 | 0.490 | 1.5201 | 59.00 |
| 11ASPH | −1.37820 | 0.200 | | |
| 12 | 0.00000 | 0.650 | 1.5187 | 64.20 |
| 13 | 0.00000 | 0.259 | | |

Aspherical surface coefficients according to the fourth example are as follows.

| No. | K | A4<br>A10 | A6<br>A12 | A8 |
|---|---|---|---|---|
| 2 | 5.13380E−02 | 1.06518E+00<br>−7.61835E+02 | −1.96640E+01<br>0.00000E+00 | 2.05247E+02 |
| 4 | −1.00000E+01 | −1.44397E+00<br>0.00000E+00 | 3.19893E+00<br>0.00000E+00 | −1.10647E+02 |
| 5 | −4.05913E+00 | −3.15234E+00<br>−2.99748E+02 | −1.72964E+00<br>8.23249E+01 | 5.65808E+01 |
| 6 | 1.00000E+01 | −8.48435E−01<br>2.72750E+03 | 1.91502E+01<br>−1.55050E+00 | −4.62189E+02 |
| 7 | −1.57461E+00 | −5.52775E−02<br>−6.17110E+01 | −9.18279E+00<br>5.37675E+01 | 1.76412E+01 |
| 8 | 1.00000E+01 | −5.82970E−01<br>5.68956E+01 | −6.78943E+00<br>4.73528E+00 | −1.79163E+01 |
| 9 | −5.47271E−01 | −6.19298E−01<br>−5.00363E+00 | −4.64407E+00<br>−5.61302E+00 | 9.61624E+00 |
| 10 | −8.53374E+00 | 7.81820E−01<br>−4.58307E+00 | −1.69202E+00<br>1.26977E+00 | 3.16721E+00 |
| 11 | −1.00000E+01 | −1.36839E−01<br>−2.14883E+00 | 8.15417E−01<br>−1.13111E+00 | 1.10727E+00 |

Fifth Example

Figure 9:
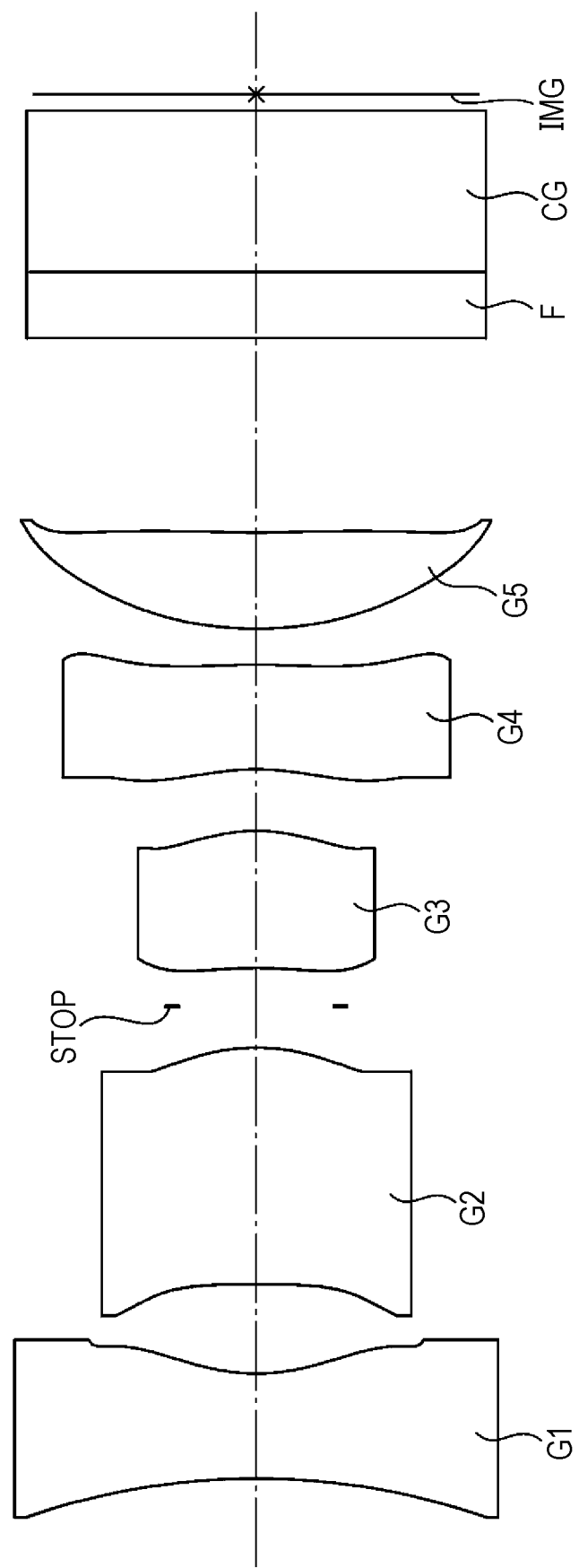
FIG. 9 illustrates an optical configuration of an imaging optical system according to a fifth example of the present invention.
Figure 10:
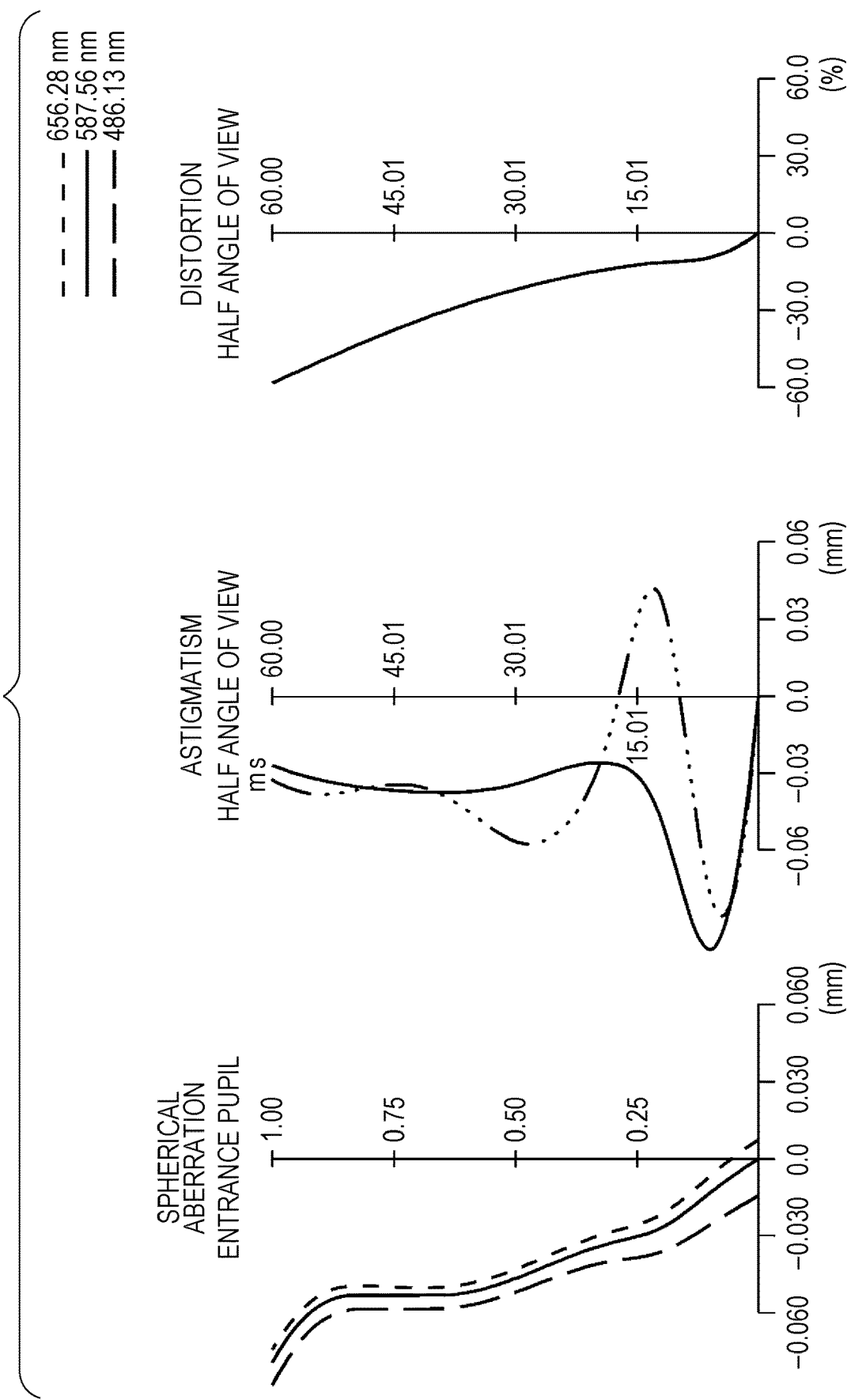
FIG. 10 is a diagram illustrating aberration of the imaging optical system according to the fifth example of the present invention.

As illustrated in FIG. 9, an imaging optical system according to a fifth example of the present invention includes, in order from the object side, a first lens G1 having negative refractive power, a second lens G2 having positive refractive power, a third lens G3 having positive refractive power, a negative fourth lens G4, and a positive fifth lens G5, as well as a filter F and a cover glass CG adhered to each other. Note that IMG indicates an imaging plane.

The fifth example is characterized in that the fifth lens G5 has negative refractive power. The third lens G3 has the refractive power larger than that in any other example with the five-lens configuration. Furthermore, the total thickness of the lens smaller than that in any other example with the five-lens configuration, and a large BF can be obtained despite the small total length.

The specification table and the focal lengths of the respective lenses according to the fifth example are as described below.

(Specification table)

| | |
|---|---|
| Focal length | 0.81407 |
| F number | 4 |
| Half angle of view (°) | 60 |
| Lens total length | 3.958 |
| BF (air equivalent) | 1.03298 |

(Focal length of each lens)

| | |
|---|---|
| f1 | −0.768 |
| f2 | 1.100 |
| f3 | 1.197 |
| f4 | −2.672 |
| f5 | −327.343 |
| f12 | 1.955 |

The surface data table of the fifth example is as follows.

(Surface data table)

| No. | r | d | nd | vd |
|---|---|---|---|---|
| 1 | −1.96760 | 0.300 | 1.5463 | 55.80 |
| 2ASPH | 0.56210 | 0.256 | | |
| 3ASPH | −6.37240 | 0.676 | 1.5207 | 50.00 |
| 4ASPH | −0.54480 | 0.117 | | |
| 5STOP | 0.00000 | 0.111 | | |
| 6ASPH | −1.19060 | 0.393 | 1.5463 | 55.80 |
| 7ASPH | −0.47120 | 0.176 | | |
| 8ASPH | −0.60640 | 0.300 | 1.6686 | 20.40 |
| 9ASPH | −1.09990 | 0.100 | | |
| 10ASPH | 1.01990 | 0.275 | 1.5202 | 56.00 |
| 11ASPH | 0.92040 | 0.557 | | |
| 12 | 0.00000 | 0.650 | 1.5187 | 64.20 |
| 13 | 0.00000 | 0.048 | | |

Aspherical surface coefficients according to the fifth example are as follows.

| No. | K | A4<br>A10 | A6<br>A12 | A8<br>A14 |
|---|---|---|---|---|
| 2 | 3.59029E−01 | −1.82949E+00<br>−2.04735E+02 | −2.39868E+01<br>0.00000E+00 | 9.31211E+01<br>0.00000E+00 |
| 3 | 2.43694E+02 | −2.98565E+00<br>0.00000E+00 | −2.22891E+01<br>0.00000E+00 | 1.50737E+02<br>0.00000E+00 |
| 4 | −4.35923E+00 | −2.35958E+00<br>2.88038E+03 | 4.98463E+01<br>8.23249E+01 | −5.27960E+02<br>−3.00364E+02 |
| 6 | −2.15155E+01 | 3.77477E+00<br>−1.46939E+03 | −7.20205E+00<br>−1.55050E+00 | 3.25653E+02<br>1.78529E+01 |
| 7 | −5.35567E+00 | 6.63789E−01<br>−1.21123E+02 | 5.18189E+00<br>5.37675E+01 | 2.04738E+02<br>−2.76606E+01 |
| 8 | −2.49901E+01 | 6.56782E−02<br>−2.34406E+02 | 1.06633E+01<br>4.73528E+00 | 2.10808E+01<br>−8.09837E+00 |
| 9 | −4.72726E+02 | 1.39761E+00<br>−5.55451E+01 | −1.93959E+00<br>−5.61302E+00 | 1.25915E+01<br>8.73337E−01 |

-continued

| No. | K | A4<br>A10 | A6<br>A12 | A8<br>A14 |
|---|---|---|---|---|
| 10 | −1.97229E+00 | 3.86329E−01<br>1.39498E+01 | 1.07148E+00<br>1.26977E+00 | −7.94900E+00<br>−1.33983E+00 |
| 11 | −1.27631E+03 | −5.33561E−01<br>2.28574E+01 | 3.11631E+00<br>−1.13111E+00 | −1.28883E+01<br>−9.28668E−01 |

Sixth Example

Figure 11:
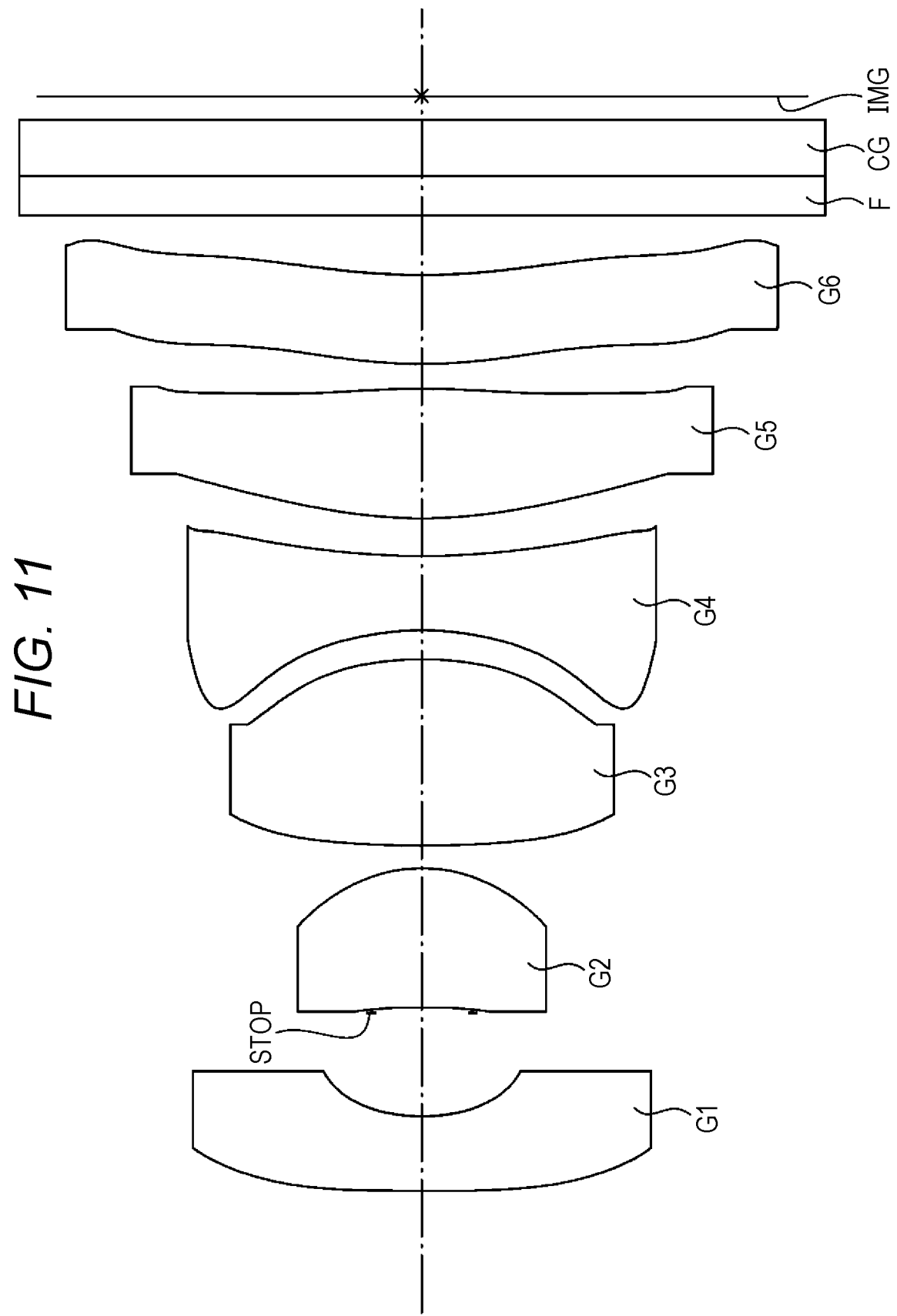
FIG. 11 illustrates an optical configuration of an imaging optical system according to a sixth example of the present invention.
Figure 12:
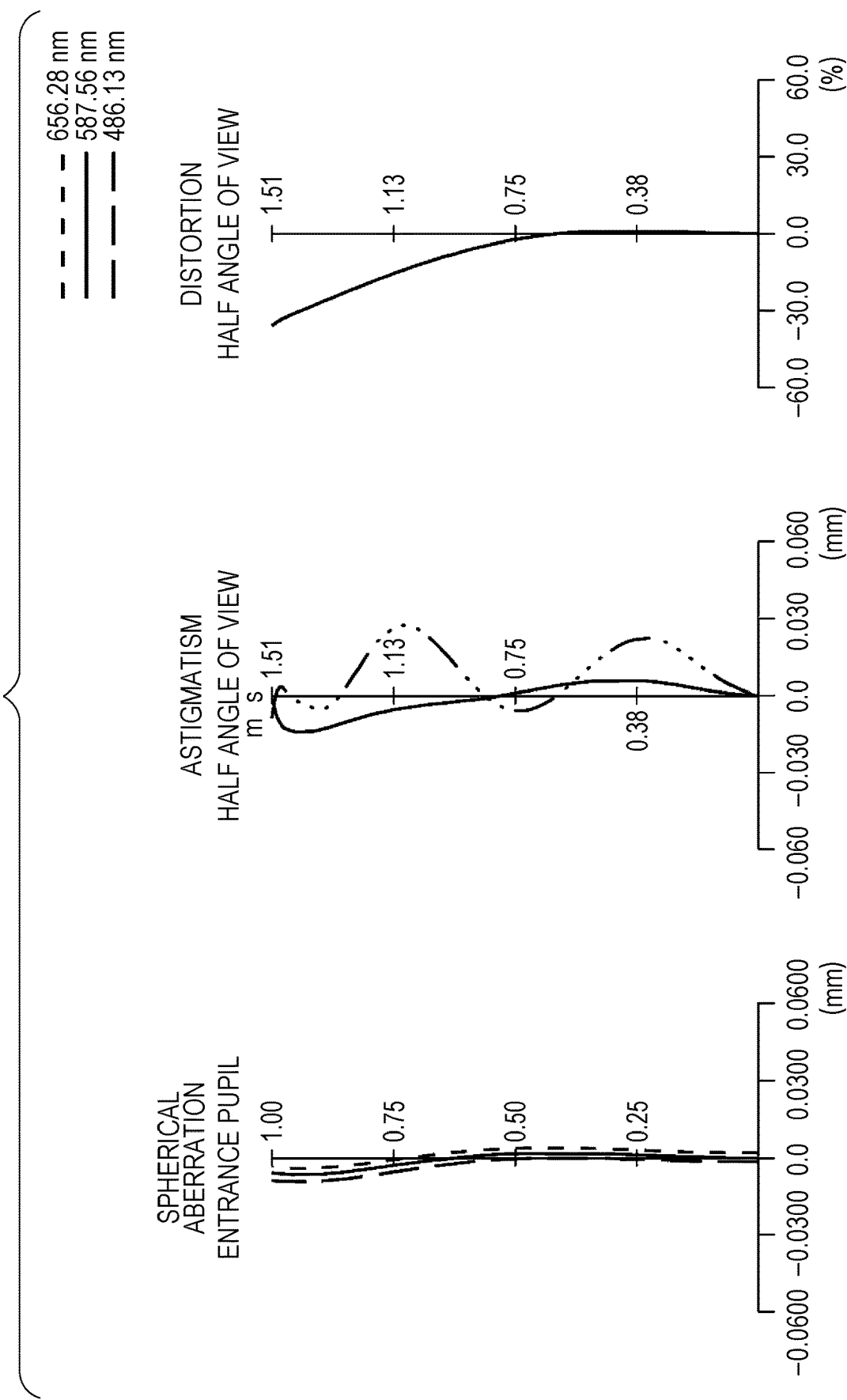
FIG. 12 is a diagram illustrating aberration of the imaging optical system according to the sixth example of the present invention.

As illustrated in FIG. 11, an imaging optical system according to a sixth example of the present invention includes, in order from the object side, a first lens G1 having negative refractive power, a second lens G2 having positive refractive power, a third lens G3 having positive refractive power, a negative fourth lens G4, a positive fifth lens G5, and a positive sixth lens G6 as well as a filter F and a cover glass CG adhered to each other. Note that IMG indicates an imaging plane.

The sixth example features a six-lens configuration. If the imaging optical system has a six-lens configuration, the principal ray having a peripheral image height passes through a position higher, with respect to the optical axis, than the fifth lens G5 in the five-lens configuration example. Thus, the configuration is effective for correcting the curvature of field, distortion, and the like at the intermediate image height. The aperture stop of the imaging optical system is provided between the image side surface of the first lens G1 and the second lens G2. With the aperture stop being provided between the image side surface of the first lens G1 and the second lens G2, the first lens G1 of the imaging optical system is downsized.

The specification table and the focal lengths of the respective lenses according to the sixth example are as described below.

(Specification table)

| Focal length | 1.07322 |
|---|---|
| F number | 4 |
| Half angle of view (°) | 64.998 |
| Lens total length | 4.414 |

-continued

| BF (air equivalent) | 0.589631 |
|---|---|

(Focal length of each lens)

| f1 | −1.282 |
|---|---|
| f2 | 1.242 |
| f3 | 1.950 |
| f4 | −1.221 |
| f5 | 2.313 |
| f12 | 1.774 |

The surface data table of the sixth example is as follows.

(Surface data table)

| No. | r | d | nd | vd |
|---|---|---|---|---|
| 1ASPH | 42.33490 | 0.300 | 1.5462 | 55.88 |
| 2ASPH | 0.68700 | 0.417 | | |
| 3STOP | 0.00000 | 0.023 | | |
| 4ASPH | −2.81220 | 0.563 | 1.5462 | 55.88 |
| 5ASPH | −0.58530 | 0.091 | | |
| 6ASPH | 4.22250 | 0.752 | 1.5462 | 55.88 |
| 7ASPH | −1.33480 | 0.117 | | |
| 8ASPH | −1.14320 | 0.300 | 1.6580 | 21.51 |
| 9ASPH | 2.98810 | 0.150 | | |
| 10ASPH | 1.96470 | 0.522 | 1.5462 | 55.88 |
| 11ASPH | −3.20620 | 0.100 | | |
| 12ASPH | 1.96320 | 0.360 | 1.6580 | 21.51 |
| 13ASPH | 2.78000 | 0.241 | | |
| 14 | 0.00000 | 0.384 | 1.5187 | 64.20 |
| 15 | 0.00000 | 0.096 | | |

Aspherical surface coefficients according to the sixth example are as follows.

| No. | K | A4<br>A10 | A6<br>A12 | A8<br>A14 |
|---|---|---|---|---|
| 1 | 1.00000E+02 | 3.64368E−01<br>4.90426E−02 | −2.79132E−01<br>−1.06373E−03 | 1.02797E−01<br>−4.80368E−09 |
| 2 | 1.79878E+00 | 7.17466E−02<br>−9.18556E+01 | 1.70466E+00<br>−1.33668E−08 | 1.36005E+01<br>−8.11677E−10 |
| 4 | −1.00000E+01 | −7.03649E−01<br>−2.07129E+02 | 2.22125E+00<br>−3.39741E−10 | −2.68535E+01<br>5.37998E−11 |
| 5 | −1.88792E−01 | 1.99652E−01<br>−3.69417E+01 | −6.13757E−01<br>4.65823E−01 | 1.31887E+01<br>−6.63341E−01 |
| 6 | 7.60415E+00 | −1.06702E−01<br>2.44783E−01 | 7.85603E−01<br>−8.78434E−03 | −7.45100E−01<br>3.94273E−02 |
| 7 | 1.72225E+00 | −1.92861E−01<br>3.31656E−01 | −9.85465E−01<br>3.04236E−01 | 2.22634E+00<br>−6.10872E−02 |
| 8 | −7.64828E+00 | −2.31578E−01<br>2.15554E+00 | −8.01018E−01<br>2.67938E−02 | −3.60203E−01<br>−1.78849E−02 |
| 9 | 8.96633E+00 | −1.79881E−01<br>−3.37113E−03 | 3.57421E−01<br>7.35477E−03 | −4.12369E−01<br>1.92874E−03 |
| 10 | 5.89908E−01 | −1.00914E−01<br>−5.77728E−02 | −8.20615E−02<br>1.01432E−03 | 1.38485E−01<br>−3.00775E−03 |

-continued

| No. | K | A4<br>A10 | A6<br>A12 | A8<br>A14 |
|---|---|---|---|---|
| 11 | 1.57774E+00 | 4.36893E−01<br>4.70344E−02 | −4.35516E−01<br>1.05043E−02 | 1.01397E−01<br>−6.03246E−04 |
| 12 | 5.88098E−01 | −2.59312E−01<br>−3.15665E−02 | −5.11969E−02<br>2.00417E−03 | 1.40545E−01<br>−4.36135E−03 |
| 13 | 2.70952E+00 | −3.96124E−02<br>−5.52975E−02 | −2.71292E−01<br>−2.30950E−03 | 2.45743E−01<br>−1.29182E−03 |

Corresponding values of the conditional expressions in each example are as follows.

(Table of corresponding values of conditional expression)

| | Example 1 | Example 2 | Example 3 | Example 4 | Example 5 | Example 6 |
|---|---|---|---|---|---|---|
| Conditional Expression (1): f2/f | 1.599 | 1.181 | 1.161 | 1.315 | 1.352 | 1.158 |
| Conditional Expression (2): f3/f | 1.633 | 1.894 | 1.586 | 1.480 | 1.470 | 1.817 |
| Conditional Expression (3): Half angle of view W | 60.000 | 60.000 | 60.000 | 60.000 | 60.000 | 64.998 |
| Conditional Expression (4): f12/f | 3.759 | 2.045 | 1.744 | 5.005 | 2.401 | 1.653 |
| Conditional Expression (5): D12/f | 0.590 | 0.553 | 0.577 | 0.384 | 0.314 | 0.409 |
| Conditional Expression (6): ν2 | 55.881 | 55.881 | 55.881 | 49.999 | 49.999 | 55.881 |
| Conditional Expression (7): OAL | 3.952 | 3.954 | 3.602 | 3.944 | 3.958 | 4.414 |
| Conditional Expression (8): D45/f | 0.123 | 0.135 | 0.123 | 0.344 | 0.123 | 0.140 |
| Conditional Expression (9): f1/f | −1.045 | −0.823 | −0.875 | −0.812 | −0.943 | −1.194 |
| Conditional Expression (10): |f4|/f | 1.479 | 1.614 | 1.076 | 1.655 | 3.282 | 1.138 |
| Conditional Expression (11): |f5|/f | 2.407 | 2.350 | 2.089 | 2.273 | 402.110 | 2.155 |
| Conditional Expression (12): RG1R2/f | 0.511 | 0.449 | 0.478 | 0.460 | 0.690 | 0.640 |
| Conditional Expression (13): RG2R2/f | −0.883 | −0.877 | −0.858 | −0.691 | −0.669 | −0.545 |
| Conditional Expression (14): RG3R2/f | −0.958 | −0.845 | −1.237 | −0.680 | −0.579 | −1.224 |
| Conditional Expression (15): OAL/f | 4.854 | 4.857 | 4.424 | 4.843 | 4.862 | 4.113 |

(Example of Image Capturing Apparatus)

Figure 13:
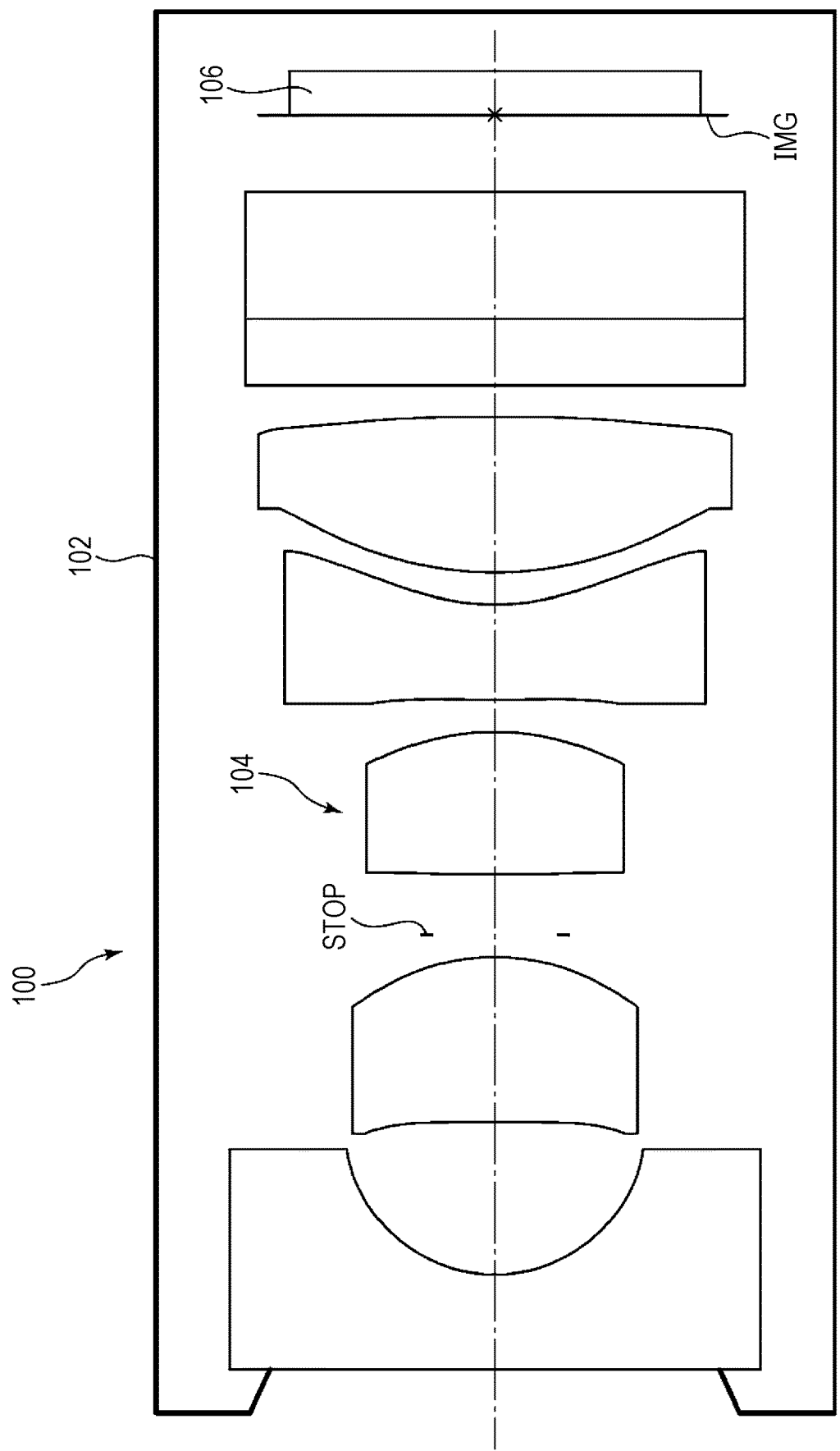
FIG. 13 illustrates a configuration of an image capturing apparatus according to an example of the present invention.

An example of an image capturing apparatus 100 includes an imaging optical system 104 and an image sensor 106 disposed on an imaging plane IMG of the imaging optical system 104 provided in an image capturing apparatus casing 102, as illustrated in FIG. 13.

What is claimed is:

1. An imaging optical system comprising, in order from an object side, a first lens having negative refractive power, a second lens having positive refractive power, a third lens having positive refractive power, a fourth lens and a fifth lens, with the fourth lens and the fifth lens not cemented, wherein following conditional expressions is satisfied:

$$1.10 \leq f2/f \leq 1.60, \text{ and} \tag{1}$$

$$1.47 \leq f3/f \leq 1.90, \tag{2}$$

where
f2 is a focal length of the second lens,
f3 is a focal length of the third lens, and
f is a focal length of the imaging optical system.

2. The imaging optical system according to claim 1, wherein following conditional expression is satisfied:

$$45.0 \leq W \leq 80.0, \tag{3}$$

where
W is a half angle of view (°).

3. The imaging optical system according to claim 1, wherein following conditional expression is satisfied:

$$0.50 \leq f12/f \leq 7.00, \tag{4}$$

where
f12 is a combined focal length of the first lens and the second lens.

4. The imaging optical system according to claim 1, wherein following conditional expression is satisfied:

$$0.10 \leq D12/f \leq 1.00, \tag{5}$$

where
D12 is a distance between the first lens and the second lens.

5. The imaging optical system according to claim 1, wherein following conditional expression is satisfied:

$$47.0 \leq \nu 2 \leq 60.0, \tag{6}$$

where
ν2 is Abbe number for d-line of the second lens.

6. The imaging optical system according to claim 1, wherein following conditional expression is satisfied:

$$3.30 \leq OAL \leq 4.35, \tag{7}$$

where
OAL is a total optical length (mm) of the imaging optical system.

7. The imaging optical system according to claim 1, wherein following conditional expression is satisfied:

$$0.08 \leq D45/f \leq 0.40, \tag{8}$$

where
D45 is a distance between the fourth lens and the fifth lens.

8. The imaging optical system according to claim 1, wherein following conditional expression is satisfied:

$$-1.30 \leq f1/f \leq -0.60, \tag{9}$$

where
f1 is a focal length of the first lens.

9. The imaging optical system according to claim 1, wherein following conditional expression is satisfied:

$$0.80 \leq |f4|/f \leq 3.60, \tag{10}$$

where
f4 is a focal length of the fourth lens.

10. The imaging optical system according to claim 1, wherein following conditional expression is satisfied:

$$1.70 \leq |f5|/f \leq 450.00, \tag{11}$$

where
f5 is a focal length of the fifth lens.

11. The imaging optical system according to claim 1, wherein following conditional expression is satisfied:

$$0.35 \leq RG1R2/f \leq 0.80, \tag{12}$$

where
RG1R2 is a radius of curvature of an image side surface of the first lens.

12. The imaging optical system according to claim 1, wherein following conditional expression is satisfied:

$$-1.20 \leq RG2R2/f \leq -0.40, \tag{13}$$

where
RG2R2 is a radius of curvature of an image side surface of the second lens.

13. The imaging optical system according to claim 1, wherein following conditional expression is satisfied:

$$-1.40 \leq RG3R2/f \leq -0.50, \tag{14}$$

where
RG3R2 is a radius of curvature of an image side surface of the third lens.

14. The imaging optical system according to claim 1, wherein the fourth lens has negative refractive power.

15. The imaging optical system according to claim 1, wherein an object side surface of the fourth lens is a concave surface.

16. The imaging optical system according to claim 1, wherein the imaging optical system has a total of five lenses with refractive power.

17. An image capturing apparatus comprising: the imaging optical system according to claim 1; and an image sensor that is provided on an imaging plane of the imaging optical system and converts an optical image formed by the imaging optical system into an electric signal.

* * * * *